(12) United States Patent
Akers et al.

(10) Patent No.: US 10,925,931 B2
(45) Date of Patent: *Feb. 23, 2021

(54) RAPID-ACTING INSULIN COMPOSITIONS

(71) Applicant: Eli Lilly and Company, Indianapolis, IN (US)

(72) Inventors: Michael Patrick Akers, Indianapolis, IN (US); Michael Edward Christe, Pendleton, IN (US); Thomas Andrew Hardy, Carmel, IN (US); Ranajoy Majumdar, Indianapolis, IN (US); Chi Arch Nguyen, Fishers, IN (US); Chad Donald Paavola, Indianapolis, IN (US); Virender Kumar Sarin, Carmel, IN (US); Nanette Elizabeth Schulte, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/868,272

(22) Filed: Jan. 11, 2018

(65) Prior Publication Data

US 2018/0140676 A1 May 24, 2018

Related U.S. Application Data

(63) Continuation of application No. 15/241,412, filed on Aug. 19, 2016, now Pat. No. 9,901,623.

(60) Provisional application No. 62/210,469, filed on Aug. 27, 2015.

(51) Int. Cl.
| | |
|---|---|
| *A61K 38/28* | (2006.01) |
| *A61K 47/12* | (2006.01) |
| *A61K 47/02* | (2006.01) |
| *A61K 47/10* | (2017.01) |
| *A61K 9/00* | (2006.01) |
| *A61K 31/192* | (2006.01) |
| *A61K 47/34* | (2017.01) |

(52) U.S. Cl.
CPC ............ *A61K 38/28* (2013.01); *A61K 9/0019* (2013.01); *A61K 31/192* (2013.01); *A61K 47/02* (2013.01); *A61K 47/10* (2013.01); *A61K 47/12* (2013.01); *A61K 47/34* (2013.01)

(58) Field of Classification Search
CPC ........................................................ A61K 38/28
See application file for complete search history.

(56) References Cited

U.S. PATENT DOCUMENTS

| | | | |
|---|---|---|---|
| 4,476,118 A | 10/1984 | Brange et al. | |
| 4,885,164 A | 12/1989 | Thurow | |
| 5,164,366 A | 11/1992 | Balschmidt et al. | |
| 5,474,978 A | 12/1995 | Bakaysa et al. | |
| 5,716,927 A | 2/1998 | Balschmidt et al. | |
| 5,866,538 A | 2/1999 | Norup et al. | |
| 5,981,594 A | 11/1999 | Okamoto et al. | |
| 7,279,457 B2 | 10/2007 | Pohl et al. | |
| 7,696,162 B2 | 4/2010 | Boderke | |
| 7,713,930 B2 | 5/2010 | Brunner-Schwarz et al. | |
| 7,879,909 B2* | 2/2011 | Wade | A61K 31/557 514/573 |
| 8,084,420 B2 | 12/2011 | Steiner et al. | |
| 8,318,154 B2 | 11/2012 | Frost et al. | |
| 8,324,157 B2 | 12/2012 | Olsen et al. | |
| 8,563,614 B2* | 10/2013 | Wade | A61K 31/557 514/569 |
| 9,439,952 B2* | 9/2016 | Christe | A61K 38/28 |
| 9,901,623 B2* | 2/2018 | Akers | A61K 31/192 |
| 10,172,922 B2* | 1/2019 | Christe | A61K 38/28 |
| 2005/0043391 A1* | 2/2005 | Fong | A61K 45/06 514/423 |
| 2005/0282903 A1 | 12/2005 | Wade et al. | |
| 2007/0086952 A1 | 4/2007 | Steiner et al. | |
| 2007/0235365 A1 | 10/2007 | Pohl et al. | |
| 2008/0090753 A1 | 4/2008 | Pohl et al. | |
| 2008/0280955 A1* | 11/2008 | McCamish | A61P 9/12 514/342 |
| 2009/0054473 A1* | 2/2009 | Roden | A61P 3/00 514/274 |
| 2009/0292245 A1* | 11/2009 | Basso | A61M 5/14212 604/122 |
| 2009/0292247 A1* | 11/2009 | Basso | F04B 23/028 604/151 |
| 2010/0167990 A1 | 7/2010 | Poulsen et al. | |
| 2010/0227795 A1 | 9/2010 | Steiner et al. | |

(Continued)

FOREIGN PATENT DOCUMENTS

| | | |
|---|---|---|
| EP | 0001124 | 3/1979 |
| EP | 214826 | 3/1987 |

(Continued)

OTHER PUBLICATIONS

Pohl et al., 2012, Ultra-Rapid Absorption of Recombinant Human Insulin Induced by Zinc Chelation and Surface Charge masking, Journal of Diabetes Science and Technology, 6(4): 755-763.*

Pandyarajan et al., 2012, Design of Non-Standard Insulin Analogs for the Treatment of Diabetes Mellitus, Curr Diab Rep, 12(6): 697-704.*

Welling et al., 2014, The role of citric acid in oral peptide and protein formulations: Relationship between calcium chelation and proteolysis inhibition, European Journal of Pharmaceuticals and Biopharmaceutics, 86: 544-551.*

(Continued)

*Primary Examiner* — Amber D Steele
(74) *Attorney, Agent, or Firm* — Matthew T Lord

(57) ABSTRACT

The invention is a pharmaceutical composition of human insulin or insulin analog that includes citrate, treprostinil and stabilizing agents, that has faster pharmacokinetic and/or pharmacodynamic action than commercial formulations of existing insulin analog products and that is stable for commercial use.

22 Claims, No Drawings

Specification includes a Sequence Listing.

(56) References Cited

U.S. PATENT DOCUMENTS

| | | | |
|---|---|---|---|
| 2010/0227796 A1* | 9/2010 | Garibay | A61P 3/10 514/6.3 |
| 2010/0249020 A1 | 9/2010 | Soula et al. | |
| 2011/0250142 A1* | 10/2011 | Fong | A61P 25/28 424/9.2 |
| 2012/0035104 A1* | 2/2012 | Kodra | A61K 38/28 514/6.3 |
| 2012/0094902 A1 | 4/2012 | Soula et al. | |
| 2012/0178675 A1 | 7/2012 | Pohl et al. | |
| 2012/0208749 A1* | 8/2012 | Garibay | A61P 3/10 514/6.3 |
| 2013/0011378 A1 | 1/2013 | Yang et al. | |
| 2013/0022592 A1 | 1/2013 | Vaughn et al. | |
| 2013/0231281 A1 | 9/2013 | Soula et al. | |
| 2013/0302275 A1 | 11/2013 | Wei et al. | |
| 2014/0113856 A1* | 4/2014 | Pohl | A61K 38/28 514/6.4 |
| 2014/0135682 A1 | 5/2014 | Frost et al. | |
| 2014/0357554 A1* | 12/2014 | Pohl | A61K 47/12 514/6.4 |
| 2015/0065423 A1 | 3/2015 | Laulicht et al. | |
| 2015/0273022 A1 | 10/2015 | Wilson et al. | |
| 2016/0166695 A1 | 6/2016 | Akers et al. | |

FOREIGN PATENT DOCUMENTS

| | | |
|---|---|---|
| EP | 280534 | 2/1988 |
| EP | 2500020 | 9/2014 |
| WO | 9733531 | 9/1997 |
| WO | 9749386 | 12/1997 |
| WO | 199934821 | 7/1999 |
| WO | 200043034 | 7/2000 |
| WO | 200135943 | 5/2001 |
| WO | 03000202 | 1/2003 |
| WO | 2003094956 | 11/2003 |
| WO | 2010023666 | 3/2010 |
| WO | 2010149772 | 12/2010 |
| WO | 2012006283 | 1/2012 |
| WO | 2012080362 | 6/2012 |
| WO | 2013158618 | 10/2013 |
| WO | 2013177565 | 11/2013 |
| WO | 2015106269 | 7/2015 |
| WO | 2015120457 | 8/2015 |
| WO | 2015171484 | 12/2015 |
| WO | 2017015760 | 2/2017 |

OTHER PUBLICATIONS

Blaise, S., et al., "Cathodal Iontophoresis of Treprostinil Induces a Sustained Increase in Cutaneous Blood Flux in Healthy Volunteers," J. Clin. Pharmacol., vol. 53, Issue 1, pp. 58-66 (2012).

Capelle, M.A.H., et al., "High Throughput Screening of Protein Formulation Stability: Practical Considerations," European Journal of Pharmaceutics and Biopharmaceutics, vol. 65, No. 2, Jan. 5, 2007, pp. 131-148.

Gille, A., et al., "Nicotinic Acid: Pharmacological Effects and Mechanisms of Action," Annu. Rev. Pharmacol. Toxicol., vol. 48, pp. 79-106 (2008).

Krasner, et al., "Lispro Formulations BIOD-238 and BIOD-250 Associated With Faster Absorption and Declines From Peak Concentrations Compared to Humalog®" available at http://files.shareholder.com/downloads/BIOD/2632769718x0x672700/BF867032-C746-4DB1-A80B-FFA9DE1E565B/Lispro_Formulations_BIOD-238_and_BIOD-250_Associated_With_Faster_Absorption_-_ADA_June_2013.PDF.

Mathier, M., et al., "Subcutaneous Treprostinil in Pulmonary Arterial Hypertension: Practical Considerations," J. Heart Lung Transplant., vol. 29, pp. 1210-1217 (2010).

McSwain, C., et al., "Dose Proportionality of Treprostinil Sodium Administered by Continuous Subcutaneous and Intravenous Infusion," J. Clin. Pharmacol., vol. 48, pp. 19-25 (2008).

Menon, R., et al., "Insulin Absorption Accelerated by α-Adrenergic Blockade at Injection Site," Diabetes Care, vol. 10, No. 4, pp. 470-472 (1987).

Moriarty, R., et al., "The Intramolecular Asymmetric Pauson-Khand Cyclization as a Novel and General Stereoselective Route to Benzindene Prostacyclins: Synthesis of UT-15 (Treprostinil)," J. Org. Chem, vol. 69, pp. 1890-1902 (2004).

Owens, D., et al., "The Influence of Aprotinin on Regional Absorption of Soluble Human Insulin," Br. J. Clin. Pharmac., vol. 25, pp. 453-456 (1988).

Pohl, R., et al., "Development of Ultra-Rapid-Acting Prandial Insulin analogs Requires Chelation of Zinc Ions and Charge Masking to Increase the Rate of Subcutaneous Absorption," available at http://files.shareholder.com/downloads/BIOD/0x0x602912/3C955886-6AA4-4D66-BD33-3FFB4C906B25/EASD_Poster_September_2012_FINAL.pdf.

Pohl, R., et al., Ultra-Rapid Absorption of Recombinant Human Insulin Induced by Zinc Chelation and Surface Charge Masking, J. Diabetes Sci Technol 2012; 6(4), pp. 755-563.

Vora, J., et al., "Relationship Between Absorption of Radiolabeled Soluble Insulin, Subcutaneous Blood Flow, and Anthropometry," Diabetes Care, vol. 15, No. 11, pp. 1484-1493 (1992).

Wade, M., et al., "Absolute Bioavailability and Pharmacokinetics of Treprostinil Sodium Administered by Acute Subcutaneous Infusion," J. Clin. Pharmacol., vol. 44, pp. 83-88 (2004).

Williams, G., et al., "Subcutaneous Aprotinin Causes Local Hyperaemia," Diabetologia, vol. 24, pp. 91-94 (1983).

Williams, G., et al., "Prostaglandin E1 Accelerates Subcutaneous Insulin Absorption in Insulin-Dependent Diabetic Patients," Diabetic Medicine, pp. 109-113 (1984).

NDA 21-272, RemodulinTM, Medical Review, available at http://www.accessdata.fda.gov/drugsatfda_docs/nda/2002/21-272_Remodulin.cfm (Jul. 31, 2002).

NDA 21-272, RemodulinTM, Clinical Pharmacology & Biopharmaceutics Review(s), available at http://www.accessdata.fda.gov/drugsatfda_docs/nda/2002/21-272_Remodulin.cfm (Jul. 31, 2002).

Patent Cooperation Treaty International Search Report and Written Opinion of the International Searching Authority pertaining to International Application No. PCT/US2015/064744; International Filing Date: Dec. 9, 2015; dated Mar. 23, 2016.

Heart View, vol. 17, No. 4, p. 53(385)-60(392), 2013.

B.J.Whittle, et al., "Binding and activity of the prostacyclin receptor (IP) agonists, treprostinil and iloprost, at human prostanoid receptors: Treprostinil is a potent $DP_1$ and $EP_2$ agonist," Biochemical Pharmacology, 84 (2012) 68-75.

Skoro-Sajer, Nika, et al., "Treprostinil for Pulmonary Hypertension," Vascular Health and Risk Management, Jan. 1, 2008, pp. 507-513.

Prabhu, S., Jacknowitz, A. I., & Stout, P. J. (2001). A study of factors controlling dissolution kinetics of zinc complexed protein suspensions in various ionic species. *International journal of pharmaceutics*, 217(1), 71-78.

REMODULIN® (treprostinil) Injection Package Insert (May 2002).

Blevins, T., et al. Randomized double-blind clinical trial comparing Ultra rapid lispro with Lispro in a basal-bolus regimen in patients with type 2 diabetes: PRONTO-T2D. *Diabetes Care.* https://doi.org/10.2337/dc19-2550 (2020).

Klaff, L., et al. Ultra Rapid Lispro Improves Postprandial Glucose Control Compared With Lispro in Patients With Type 1 Diabetes: Results from the 26-Week PRONTO-T1D Study. *Diabetes, Obesity and Metabolism.* doi: 10.1111/dom.14100 (2020).

\* cited by examiner

SEQUENCE LISTING

<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30

RAPID-ACTING INSULIN COMPOSITIONS

This application is a continuation of U.S. application Ser. No. 15/241,412 (now U.S. Pat. No. 9,901,623), filed Aug. 19, 2019, which claims priority to U.S. Provisional Application No. 62/210,469 filed Aug. 27, 2015.

The present invention is a pharmaceutical composition for use in the treatment of diabetes to counteract postprandial blood glucose excursions and for acute treatment of hyperglycemia. The composition, which includes human insulin or an insulin analog, citrate, treprostinil and stabilizing agents, has a faster uptake of insulin from injection sites than existing commercial insulin compositions and that is stable for commercial use. The composition is useful for providing meal-time insulin activity, for use in continuous subcutaneous insulin infusion (CSII) or as an acute treatment for hyperglycemia when insulin is needed.

The time-action profile of insulin is important for controlling postprandial blood glucose levels. In healthy individuals, the pancreas secretes a spike of insulin in response to absorbed food, which results in increased plasma insulin levels within several minutes. In individuals with type 1 diabetes and in certain individuals with type 2 diabetes, insulin must be administered; however, administered insulin enters blood slowly from the subcutaneous space. Delayed release of insulin and onset of action which is too slow at the beginning of a meal leads to hyperglycemia during or immediately after the meal. A protracted duration of action from the subcutaneous space leads to excessive insulin between meals which can cause postprandial hypoglycemia.

There have been previous efforts to accelerate the time action of insulin products. Early efforts to develop such products included the development of novel rapid-acting insulin analogs, like insulin lispro (HUMALOG®), insulin aspart (NOVOLOG®), and insulin glulisine (APIDRA®). Insulin lispro and insulin aspart achieve rapid action through changes in the amino acid sequences from human insulin that weaken the dimer-dimer interface and alter hexameric stability under subcutaneous conditions. Insulin glulisine also includes changes in the sequences of the amino acid chains in human insulin; however, its commercial formulation lacks zinc and does not form stabilizing hexamers. Another insulin analog stated to be rapid-acting, but which is still in development, Fluorolog, includes a single fluorine atom attached to the Phe residue at position 24 of the insulin B-chain.

The rapid-acting insulin analogs insulin lispro, aspart and glulisine became available in the 1990s and early 2000s. Even with so-called rapid-acting insulin analogs, however, the maximum plasma insulin level is not reached until 50-90 minutes following a subcutaneous injection. This is slower than endogenous insulin release from a normally functioning pancreas and does not always match glucose absorption profiles.

Another avenue to achieve rapid action that has been explored is the use of ingredients or excipients which improve the time action profile of insulin when provided in combination with insulin. For example, U.S. Pat. No. 8,324,157 states that a faster onset of action compared with existing insulin therapies can be achieved by adding a nicotinic compound, such as nicotinamide, and the amino acid arginine, and optionally glutamic acid. US2013/0231281 discloses compositions comprising an insulin and oligosaccharides, either alone or in combination with a polyanionic compound and states that such compositions are fast acting. US2014/0113856 discloses compositions containing insulin in combination with a zinc chelator, such as ethylenediaminetetraacetic acid (EDTA), another excipient described in the publication as a "dissolution/stabilization" agent, such as citric acid or sodium citrate, and a magnesium-containing compound, and states that such compositions have more rapid absorption rates and declines from peak concentrations. US2015/0065423 describes compositions comprising a peptide and a vasodilatory agent, discloses lists of vasodilatory agents from three different categories, and provides data on compositions containing insulin lispro and nitroglycerin and states that such formulations are rapid acting.

Despite these and other efforts, a need remains for insulin compositions that have more rapid uptake of insulin into the blood from the injection site, more rapid onset and/or offset of action than existing insulin products, and chemical and physical stability during storage and use conditions. The present invention seeks to provide compositions which meet one or more of these needs.

It has surprisingly been found that compositions containing certain concentrations of both citrate and treprostinil have a more rapid time action profile than existing commercially available insulin compositions, and that the chemical and physical stability of the compositions containing those concentrations of both citrate and treprostinil can be maintained, without eliminating the improvements in time action, by including in the compositions zinc and one or more additional stabilizing agents such as a surfactant, magnesium chloride or sodium chloride.

Accordingly, the present invention provides pharmaceutical compositions comprising: an insulin; citrate, in a concentration from about 5 to about 25 mM; treprostinil, in a concentration from about 0.04 to about 20 µg/mL; zinc, in a concentration sufficient to provide at least 2 zinc ions per six molecules of insulin; a preservative; and one or more additional stabilizing agents; and having a pH of about 7.0 to about 7.8 at room temperature.

In certain embodiments, the pharmaceutical composition comprises insulin lispro, in a concentration from about 100 to about 200 U/mL; citrate, in a concentration from about 15 to about 25 mM; treprostinil, in a concentration from about 0.5 to about 2 µg/mL; zinc, in a concentration from about 0.2 to about 1 mM; m-cresol, in a concentration from about 2.5 to about 3.8 mg/mL; poloxamer 188, in a concentration from about 0.03 to about 0.12 w/v; magnesium chloride, in a concentration resulting in a molar ratio of magnesium chloride to citrate of about 1:3; glycerol, in a concentration from about 1 to about 2 mg/mL; and has a pH from about 7.0 to about 7.8 at room temperature.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; poloxamer 188, in a concentration of about 0.09% w/v; magnesium chloride, in a concentration of about 5 mM; m-cresol, in a concentration of about 3.15 mg/mL; glycerol, in a concentration of about 1.61 mg/mL; and has a pH of about 7.4.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; poloxamer 188, in a concentration of about 0.06 to 0.12% w/v; magnesium chloride, in a concentration of about 5 mM; m-cresol, in a concentration of about 3.15 mg/mL; glycerol, in a concentration of about 1.61 mg/mL; and has a pH of about 7.4.

In certain embodiments, the pharmaceutical composition comprises insulin lispro, in a concentration from about 100 to about 200 U/mL; citrate, in a concentration from about 15 to about 25 mM; treprostinil, in a concentration from about 0.5 to about 2 µg/mL; and zinc, in a concentration from about 0.2 to about 2 mM.

In certain embodiments, the pharmaceutical composition comprises insulin lispro, in a concentration from about 100 to about 200 U/mL; citrate, in a concentration from about 15 to about 25 mM; treprostinil, in a concentration from about 0.5 to about 2 µg/mL; zinc, in a concentration from about 0.2 to about 2 mM; and magnesium, in a concentration resulting in a molar ratio of magnesium to citrate of about 1:1 to about 1:5.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; and magnesium, in a concentration of about 5 mM.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; magnesium, in a concentration of about 5 mM; and m-cresol, in a concentration of about 3.15 mg/mL.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; magnesium, in a concentration of about 5 mM; m-cresol, in a concentration of about 3.15 mg/mL; and glycerol, in a concentration of about 12 mg/mL.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; magnesium, in a concentration of about 5 mM; m-cresol, in a concentration of about 3.15 mg/mL; and a total chloride concentration of about 10 to about 50 mM; and has a pH of about 7.4

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; magnesium, in a concentration of about 5 mM; m-cresol, in a concentration of about 3.15 mg/mL; glycerol, in a concentration of about 12 mg/mL; and a total chloride concentration of about 10 to about 50 mM.

In certain embodiments, the pharmaceutical composition comprises: insulin lispro, in a concentration of about 100 U/mL; citrate, in a concentration of about 15 mM; treprostinil, in a concentration of about 1 µg/mL; zinc, in a concentration of about 0.6 mM; magnesium, in a concentration of about 5 mM; m-cresol, in a concentration of about 3.15 mg/mL; glycerol, in a concentration of about 12 mg/mL; and a total chloride concentration of about 10 to about 50 mM; and has a pH of about 7.4.

In certain embodiments, the pharmaceutical composition comprises insulin lispro, in a concentration of about 100 U/mL; citrate, in a concentration of 15 mM; treprostinil, in a concentration of 1 µg/mL; zinc, in a concentration of about 0.3 mM; phosphate, in a concentration of about 7 mM; glycerol, in a concentration of about 16 mg/mL at pH 7.4.

In certain embodiments, the pharmaceutical composition comprises: insulin lispro, in a concentration of about 200 U/mL; citrate, in a concentration of about 15 mM; treprostinil, in a concentration of about 1 µg/mL; and zinc, in a concentration of about 0.7 to about 1.7 mM.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; and magnesium in a concentration of about 5 to about 10 mM.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; and magnesium in a concentration of about 5 mM.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; and a total chloride concentration of about 10 to about 50 mM.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; and glycerol in a concentration of about 12 mg/mL.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; glycerol in a concentration of about 12 mg/mL; and a total chloride concentration of about 10 to about 50 mM.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.7 to about 1.7 mM; and m-cresol, in a concentration of about 3.15 mg/mL.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; and m-cresol in a concentration of about 3.15 mg/mL.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; a total chloride concentration of about 10 to about 50 mM; and m-cresol, in a concentration of about 3.15 mg/mL.

In certain embodiments, the pharmaceutical composition comprises: insulin lispro, in a concentration of about 200 U/mL; citrate, in a concentration of about 15 mM; treprostinil, in a concentration of about 1 µg/mL; zinc, in a concentration of about 0.8 mM; magnesium in a concentration of about 5 to about 10 mM; glycerol in a concentration of about 12 mg/mL; and m-cresol, in a concentration of about 3.15 mg/mL.

In certain embodiments, the pharmaceutical composition comprises: insulin lispro, in a concentration of about 200 U/mL; citrate, in a concentration of about 15 mM; treprostinil, in a concentration of about 1 μg/mL; zinc, in a concentration of about 0.8 mM; magnesium in a concentration of about 5 to about 10 mM; glycerol in a concentration of about 12 mg/mL; and a total chloride concentration of about 10 to about 50 mM; and m-cresol, in a concentration of about 3.15 mg/mL.

In certain embodiments, the pharmaceutical composition comprises: insulin lispro, in a concentration of about 200 U/mL; citrate, in a concentration of about 15 mM; treprostinil, in a concentration of about 1 μg/mL; zinc, in a concentration of about 0.8 mM; magnesium in a concentration of about 5 mM; glycerol in a concentration of about 12 mg/mL; and a total chloride concentration of about 10 to about 50 mM; and m-cresol, in a concentration of about 3.15 mg/mL.

In addition, the present invention also provides a method of treating diabetes comprising administering to a human in need thereof an effective dose of a pharmaceutical composition of the present invention.

In addition, the present invention provides a pharmaceutical composition for use in therapy. More particularly, the present invention provides a pharmaceutical composition for use in the treatment of diabetes. The present invention also provides the use of a pharmaceutical composition in the manufacture of a medicament for the treatment of diabetes.

In addition, the present invention provides an article of manufacture comprising a pharmaceutical composition. More particularly, in certain aspects the article of manufacture is a multi-use vial, a cartridge, a re-usable pen injector, a disposable pen device, a pump device for continuous subcutaneous insulin infusion therapy or a container closure system for use in a pump device for continuous subcutaneous insulin infusion therapy.

When used herein, the term "composition" refers to a combination of insulin and the other ingredients or excipients wherein the insulin and other ingredients or excipients are in a single combined formulation, typically an aqueous formulation.

When used herein, "insulin" means human insulin or a rapid-acting structural variant, mutein, or analog of human insulin that has the functional activity of but faster onset of action than human insulin. Particular rapid-acting analogs of human insulin are insulin lispro, insulin aspart, and insulin glulisine. Insulin for commercial products may be produced using recombinant DNA methods or by chemical synthesis. Recombinant methods are well-known and are strongly preferred. A molecule of human insulin (CAS No. 11061-68-0) consists of two amino acid chains, A and B, whose sequences are well-known.

The human insulin A-chain has the following sequence of amino acids:

(SEQ ID NO: 1)
Gly Ile Val Glu Gln Cys Cys Thr Ser Ile Cys

Ser Leu Tyr Gln Leu Glu Asn Tyr Cys Asn.

The human insulin B-chain has the following sequence of amino acids:

(SEQ ID NO: 2)
Phe Val Asn Gln His Leu Cys Gly Ser His Leu

Val Glu Ala Leu Tyr Leu Val Cys Gly Glu Arg

Gly Phe Phe Tyr Thr Pro Lys Thr.

The chains are joined by two disulfide bonds: CysA7-CysB7 and CysA20-CysB19.

The A-chain has an intra-chain disulfide bond at CysA6-CysA11. Human insulin has the empirical formula $C_{257}H_{383}N_{65}O_{77}S_6$ and a molecular weight of 5808.

Insulin lispro, the drug substance in HUMALOG®, is identical to human insulin in terms of its primary amino acid sequence except for an inversion of the natural proline-lysine sequence on the B-chain at positions 28 and 29 ($28^B$-L-Lysine-$29^B$-L-proline human insulin). Insulin lispro (CAS No. 133107-64-9) has been shown to be equipotent to human insulin on a molar basis but its effect after subcutaneous injection is more rapid and of shorter duration than that of injected soluble human insulin. HUMALOG® contains m-cresol as a preservative and a stabilizing agent, a tonicity modifier (glycerol), a buffering agent (dibasic sodium phosphate), a stabilizer (zinc oxide) and pH adjustment for the vehicle.

A molecule of insulin lispro consists of the human insulin A-chain (SEQ ID NO. 1) cross-linked with the insulin lispro B-chain, whose amino acid sequence is given by SEQ ID NO:3, below:

(SEQ ID NO: 3)
Phe Val Asn Gln His Leu Cys Gly Ser His Leu

Val Glu Ala Leu Tyr Leu Val Cys Gly Glu Arg

Gly Phe Phe Tyr Thr Lys Pro Thr.

The chemical formula of insulin lispro is $C_{257}H_{383}N_{65}O_{77}S_6$ and its molecular weight is approximately 5808. One unit of insulin lispro is equivalent to 0.0347 mg insulin lispro.

Insulin aspart (CAS No. 116094-23-6), the drug substance in NOVOLOG®, is another rapid-onset insulin analog. Its structure consists of the A-chain of human insulin (SEQ ID NO: 1) and a B-chain in which the Pro at B28 is replaced with Asp (Pro-B28-Asp human insulin), as reflected in the following amino acid sequence:

(SEQ ID NO: 4)
Phe Val Asn Gln His Leu Cys Gly Ser His Leu

Val Glu Ala Leu Tyr Leu Val Cys Gly Glu Arg

Gly Phe Phe Tyr Thr Asp Lys Thr.

Insulin aspart ($28^B$ aspartic acid-human insulin) has the empirical formula $C_{256}H_{381}N_{65}O_{79}S_6$ and a molecular weight of about 5826. One unit of insulin aspart corresponds to 6 nmol, corresponding with 0.035 mg salt-free anhydrous insulin aspart.

Insulin glulisine (CAS No. 207748-29-6), the drug substance in APIDRA®, is yet another rapid-onset insulin analog. A molecule of insulin glulisine consists of human insulin A-chain (SEQ ID NO: 1) and a modified B-chain (Asn-B3-Lys, Lys-B29-Glu) compared with human insulin, as reflected in the following amino acid sequence:

```
                                         (SEQ ID NO: 5)
Phe Val Lys Gln His Leu Cys Gly Ser His Leu

Val Glu Ala Leu Tyr Leu Val Cys Gly Glu Arg

Gly Phe Phe Tyr Thr Pro Glu Thr.
```

Insulin glulisine ($3^B$-lysine-$29^B$-glutamic acid-human insulin) has the empirical formula $C_{258}H_{384}N_{64}O_{78}S_6$ and a molecular weight of 5823. One unit of insulin glulisine corresponds approximately to 0.0349 mg of insulin glulisine.

The following scheme depicts the amino acid sequences and disulfide bonds of human insulin and of the rapid-acting insulin analogs that are presently approved for use in treating meal-time excursions of blood glucose:

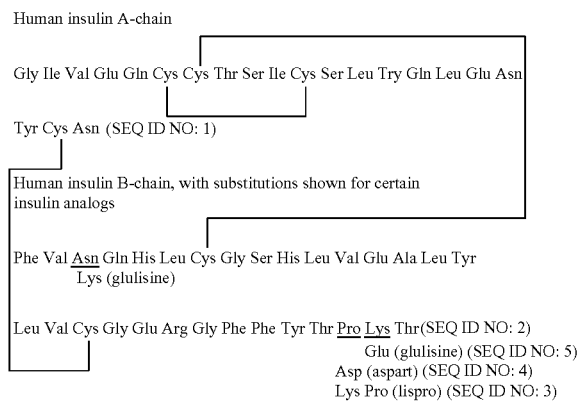

In certain embodiments, the compositions of the present invention have concentrations of insulin from about 40 to about 500 U/mL. In certain embodiments, the compositions of the present invention have concentrations of insulin from about 100 to about 500 U/mL. In certain embodiments, the compositions of the present invention have concentrations of insulin from about 100 to about 300 U/mL. In certain embodiments, the compositions of the present invention have concentrations of insulin from about 100 to about 200 U/mL. In certain preferred embodiments, the compositions comprise about 100 U/mL or about 200 U/mL.

In an embodiment, the insulin is selected from the group consisting of human insulin, or a rapid-acting structural variant, mutein, or analog of human insulin, such as insulin lispro, insulin aspart or insulin glulisine. In a preferred embodiment, the insulin is insulin lispro.

The improvements in the time action profile of the insulin demonstrated in the present invention are achieved through the use of certain specific concentrations of citrate and treprostinil.

The term "citrate" refers to any compound containing the citrate ion, which has the chemical name 2-hydroxypropane-1,2,3-tricarboxylate, molecular formula $C_6H_5O_7^{-3}$, and molecular weight of 189. The citrate ion is widely distributed in plants and animals and is a naturally occurring component of the diet. It is a common metabolite in oxidative metabolism and an important component of bone. A number of citrates are GRAS (generally regarded as safe) by the U.S. Food and Drug Administration for use in foods, including the following:

| GRAS Substance | Formula (m.w.) | CAS No. | 21 CFR |
|---|---|---|---|
| Citric acid | $C_6H_8O_7$ (192.12) | 77-92-9 | 184.1033 |
| Sodium citrate | $C_6H_5Na_3O_7$ (258.07) | 68-04-2 | 184.1751 |
| Potassium citrate monohydrate | $C_6H_5O_7K_3$ (324.41) | 6100-05-6 | 184.1625 |

Various citrate-containing compounds are also included in parenteral drug products according to the U.S. Food and Drug Administration Inactive Ingredients database, including for example, citric acid, citric acid monohydrate, citric acid anhydrous, sodium citrate, anhydrous trisodium citrate, trisodium citrate dihydrate. The particular citrate compound used in the compositions of the present invention may be the acidic form or various salt forms, especially the alkali (e.g., sodium and potassium) salts and/or mono or dihydrates thereof. Of these, sodium citrate is preferred.

It has been found that the concentration of citrate which may be used in compositions that are both fast acting and stable ranges from about 5 to about 25 mM. Certain compositions have citrate concentrations of about 15, about 20 or about 25 mM. It has been found that higher concentrations of citrate may lead to greater improvements in time action, but also may lead to greater liabilities from a stability standpoint. Thus, compositions with citrate concentrations at the upper end of the range require additional stabilizing agents in order to have chemical and physical stability for long-term storage and use, as described in more detail below.

Treprostinil is a synthetic analog of prostacyclin, and has the chemical name (1R,2R,3aS,9aS)-[[2,3,3a,4,9,9a-Hexahydro-2-hydroxy-1-[(3S)-3-hydroxyoctyl]-1H-benz[f]inden-5-yl]oxy]acetic acid (CAS No. 81846-19-7), molecular weight of 390.52 and a molecular formula of $C_{23}H_{34}O_5$. Treprostinil is the active ingredient in the commercial drug products sold under the trade names Remodulin®, Tyvaso® and Orenitran™, which are indicated for the treatment of pulmonary arterial hypertension to diminish symptoms associated with exercise (Remodulin®) and to improve exercise ability (Tyvaso® and Orenitran™). Tyvaso® and Orenitran™ are, respectively, inhalation and oral dosage forms, and Remodulin® is indicated for subcutaneous or intravenous use as a continuous infusion. Remodulin® is currently available in 1, 2.5, 5 and 10 mg/mL dosage strengths, and each mL contains 3 mg m-cresol, 6.3 mg sodium citrate, either 5.3 mg (1, 2.5 and 5 mg/mL strengths) or 4.0 mg (10 mg/mL strength strength) sodium chloride, and water for injection.

Like citrate, treprostinil is included to contribute to the improvement in the time action profile of the insulin. Unlike citrate, however, an increase in the concentration of treprostinil has not been found to have a negative impact on stability. Due to treprostinil's potent vasodilatory effects, however, the concentration of treprostinil in compositions of the present invention must not be so high as to cause undesired systemic effects.

Moreover, the amount of insulin, and thus the volume of the composition, administered to a given subject at a given time is titrated based upon the subject's blood glucose levels and/or anticipated carbohydrate intake. As a result, the total quantity of treprostinil provided will vary from injection to injection. For example, in some circumstances a diabetic may wish to have as little as 1 unit of insulin administered, which would be a total injection volume of just 10 μL from a 100 U/mL insulin lispro composition. On the other hand, currently available injection devices provide for doses as high as 80 U in a single injection—the total volume of such a dose from a 100 U/mL composition would be over an order of magnitude higher than that of the 1 unit dose, and some type 2 diabetes patients may require a dose of more than 100 insulin units, usually requiring more than one injection.

Thus, in compositions wherein insulin and treprostinil are both present in a single combined formulation, the treprostinil concentration must be sufficient to contribute to improvements in time action, even when a relatively small dose of insulin is needed, but must not be so high as to cause undesired systemic effects when a relatively high dose of insulin is needed. In certain embodiments, the composition comprises treprostinil in a concentration from about 0.1 to about 50 µM, or about 0.04 to about 20 µg/mL. In certain embodiments, the composition comprises treprostinil in a concentration from about 0.04 to about 10 µg/mL. A preferred treprostinil concentration in insulin compositions having insulin concentrations ranging from about 100 to about 200 U/mL is from about 0.5 to about 2 µg/mL. In certain embodiments, the treprostinil concentration is about 1 µg/mL.

As described above, while the addition of citrate leads to improvements in time action, it may also contribute to greater liabilities from a stability standpoint. Thus, the compositions of the present invention require one or more stabilizing agents above and beyond those included in currently available commercial formulations of rapid acting insulin analogs, such as excess zinc, surfactants, magnesium-containing compounds, such as magnesium chloride, and chloride-containing compounds, such as magnesium chloride and/or sodium chloride.

With regards to zinc, the compositions of the present invention must, at a minimum, include zinc in a concentration provides at least enough zinc ions for the insulin molecules to form stabilizing hexamers, which have 2 specific, high affinity zinc binding sites. See, e.g., BioMetals 18:295-303 (2005), available at http://rd.springer.com/article/10.1007/s10534-005-3685-y. The zinc ions incorporated into such insulin hexamers are sometimes referred to as "bound" zinc. Thus, the compositions of the present invention must include sufficient zinc to provide at least 2 ions of zinc per hexamer of insulin. In certain embodiments of the present invention having, for example, insulin concentrations of about 100 U/mL, about 200 U/mL, about 300 U/mL or about 500 U/mL, the minimum zinc concentration necessary to provide 2 ions of zinc per insulin hexamer would be about 0.2 mM, about 0.4 mM, about 0.6 mM or about 1 mM, respectively.

The inclusion of excess zinc—i.e., more zinc than would be bound in the 2 specific, high affinity zinc binding sites in insulin hexamers described above—however may be used to further stabilize the composition. Such zinc is sometimes referred to as "free" or "unbound" zinc. Currently available zinc-containing formulations include between about 2 and 4 zinc ions per hexamer of insulin. For example, the 100 U/mL formulations of insulin lispro (HUMALOG®) and insulin aspart (NOVOLOG®) have about 3 ions of zinc per six molecules of insulin, which corresponds with a concentration of about 0.3 mM. The currently available 200 U/mL formulation of HUMALOG® has about 3.5 ions of zinc per six molecules of insulin, which corresponds with a zinc concentration of about 0.7 mM. The currently available 100 U/mL formulation of human insulin sold by Eli Lilly and Company (HUMULIN® R) contains about 2.3 ions of zinc per six molecules of insulin, which corresponds with a zinc concentration of about 0.23 mM.

In certain compositions of the present invention, the inclusion of excess free or unbound zinc—i.e., zinc which is not bound in the 2 specific, high affinity zinc binding sites in insulin hexamers described above—has been found to have a stabilizing effect. Compositions having about 100 U/mL of insulin lispro and zinc concentrations up to about 1 mM—which would constitute about 0.2 mM bound and about 0.8 mM unbound or free zinc—have been found to be both fast acting and stable. The inclusion of too much free or unbound zinc, however, may attenuate the improvements in time action. For example, a composition having about 100 U/mL of insulin lispro with a zinc concentration of about 5 mM—which would constitute about 4.8 mM unbound zinc—was found to not have the improvements in time action seen in compositions with lower zinc concentrations. In certain embodiments, the concentration of zinc ranges from about 0.2 to about 2 mM, about 0.3 to about 1.7 mM, about 0.7 to about 1.7 mM, about 0.4 to about 1 mM, about 0.4 to about 0.8 mM or about 0.6 to about 0.9 mM. In certain embodiments the composition of zinc is about 0.3, about 0.4, about 0.5, about 0.6, about 0.7, about 0.8, about 0.9, about 1, about 1.25 or about 1.7 mM. In certain embodiments comprising about 100 U/mL insulin lispro, the concentration of zinc is about 0.6 mM. In certain embodiments comprising about 200 U/mL insulin lispro, the concentration of zinc is about 0.8 mM.

Another stabilizing agent which may be used is a surfactant. Examples of surfactants disclosed for use in parenteral pharmaceutical compositions include polysorbates, such as polysorbate 20 (TWEEN® 20), polyethylene glycols such as PEG 400, PEG 3000, TRITON™ X-100, polyethylene glycols such as polyoxyethylene (23) lauryl ether (CAS Number: 9002-92-0, sold under trade name BRIJ®), alkoxylated fatty acids, such as MYRJ™, polypropylene glycols, block copolymers such as poloxamer 188 (CAS Number 9003-11-6, sold under trade name PLURONIC® F-68) and poloxamer 407 (PLURONIC® F127), sorbitan alkyl esters (e.g., SPAN®), polyethoxylated castor oil (e.g., KOLLIPHOR®, CREMOPHOR®) and trehalose and derivatives thereof, such as trehalose laurate ester. In certain embodiments, the surfactant is selected from the group consisting of polyoxyethylene (23) lauryl ether, poloxamer 188 and trehalose laurate ester. Most preferred is poloxamer 188. In certain embodiments, the concentration of surfactant ranges from about 0.003 to about 2% w/v, about 0.003 to about 0.3% w/v or about 0.01 to about 0.2% w/v. In preferred embodiments wherein the surfactant is poloxamer 188, the concentration of poloxamer 188 ranges from about 0.06 to about 0.12 w/v. In certain embodiments, the concentration of poloxamer 188 is about 0.06% w/v. In other embodiments, the concentration of poloxamer 188 is about 0.09% w/v. In other embodiments, the concentration of poloxamer 188 is about 0.12% w/v.

Another stabilizing agent which may be used in compositions of the present invention is magnesium, which may be provided for example through the addition of a magnesium-containing compound such as magnesium chloride, which has a molecular formula of $MgCl_2$ and molecular weight of 95.211. While $MgCl_2$ may have stabilizing effects in certain compositions, high chloride ion ($Cl^-$) concentrations may result in insulin crystallization at low temperatures, and magnesium ($Mg^{+2}$) concentrations which exceed the concentration of citrate will result in insulin precipitation. Thus, the maximum amount of magnesium chloride that may be included is limited by the amount of citrate that is included. In certain embodiments, when $MgCl_2$ is used to provide magnesium as a stabilizing agent in the compositions of the present invention, the molar ratio of magnesium chloride to citrate ranges from about 1:2 to about 1:10. In certain embodiments the ratio of magnesium ranges from about 1:1 to about 1:5. Preferably the molar ratio of magnesium chloride to citrate ranges from about 1:3 to about 1:5. In certain embodiments, the concentration of magnesium ranges from about 1 about 15 mM. In certain embodiments, the concentration of magnesium ranges from about 1 about 5 mM, about 5 to about 10 mM or about 10 to about 15 mM. In certain embodiments, the concentration of magnesium is about 2.5, about 5, about 7.5 or about 10 mM.

Another stabilizing agent which may be used in compositions of the present invention is a chloride-containing compound, such as sodium chloride, which has molecular formula NaCl and molecular weight of 58.44. Sodium chloride is used in some currently available formulations of rapid acting insulin analogs, such as APIDRA® (insulin glulisine), which comprises 5 mg/mL sodium chloride and NOVOLOG® (insulin aspart), which comprises 0.58 mg/mL sodium chloride. In certain embodiments of the present invention wherein sodium chloride is used as a stabilizing agent, the concentration of sodium chloride ranges from about 1 to about 50 mM. In certain embodiments of the present invention wherein sodium chloride is used as a stabilizing agent, the concentration of sodium chloride ranges from about 10 to about 40 mM. In certain embodiments, the concentration of sodium chloride ranges from about 15 to about 25 mM. In certain embodiments, the concentration of sodium chloride is about 1, about 2, about 3, about 4, about 5, about 6, about 7, about 8, about 9, about 10, about 11, about 12, about 13, about 14, about 15, about 16, about 17, about 18, about 19 or about 20 mM.

Both $MgCl_2$ and NaCl result in the addition of chloride ($Cl^-$) ions, and if the total chloride content of the composition is too high, the insulin in the composition may crystallize at low temperatures and may also lead to instability at high temperatures. Thus, if $MgCl_2$ and/or NaCl are used as stabilizing agents, the total chloride content of the composition must be taken into consideration. Determining the total chloride amount present in the composition if $MgCl_2$ and/or NaCl are used as stabilizing agents must also take into consideration the fact that chloride ions may also be added to the composition through the addition of other components, for example with the insulin bulk active pharmaceutical ingredient (API), through the addition of small amounts of HCl which may be necessary for pH adjustments, and/or in connection with the provision of Zn, which may be added in the form of a solution prepared by solubilizing zinc oxide (ZnO) with HCl. Thus, the total chloride concentration from all sources must be considered if $MgCl_2$ and/or NaCl are to be used as stabilizing agents. In terms of concentrations, low temperature insulin crystallization has been observed in compositions containing about 100 mM NaCl, but such issues were not observed in compositions containing up to about 30 mM total chloride. In addition, the low temperature crystallization issues associated with relatively high chloride concentrations have also been found to be sensitive to citrate concentrations. Thus, compositions of the present invention having citrate concentrations at the lower end of the range provided for herein may be more tolerant of relatively higher chloride concentrations than compositions having citrate concentrations at the higher end of the range provided for herein. For example, the addition of sodium chloride concentrations as high as 50-75 mM to formulations containing 25 mM citrate have been observed to lead to low temperature crystallization issues, but such issues are not consistently observed either when 50 mM sodium chloride is added to a 15 mM citrate formulation or when 25 mM sodium chloride is added to a 25 mM citrate formulation. The total chloride added through the use of NaCl and/or $MgCl_2$ as stabilizing agents should not be more than about 50 mM. In certain embodiments of the present invention, the total chloride concentration, from all sources, ranges from about 10 to about 50 mM. In certain embodiments, the total chloride concentration ranges from about 13 to about 45 mM. In certain embodiments, the total chloride concentration ranges from about 20 to about 25 mM. In certain embodiments, the total chloride concentration ranges from about 15 to about 35 mM. In certain embodiments, the total chloride concentration ranges from about 20 to about 25 mM. In certain embodiments, the total chloride concentration is about 15 mM, about 16 mM, about 17 mM, about 18 mM, about 19 mM, about 20 mM, about 21 mM, about 22 mM, about 23 mM, about 24 mM or about 25 mM.

In certain embodiments, the composition may include more than one additional stabilizing agent in order to ensure the composition maintains a commercially acceptable stability profile. A preferred combination of stabilizing agents which may be used in compositions of the present invention includes excess zinc and magnesium. Another preferred combination of stabilizing agents which may be used in compositions of the present invention includes zinc, a surfactant, such as poloxamer 188, and magnesium chloride or sodium chloride.

The compositions of the present invention include one or more preservatives, which provide anti-microbial properties and may further provide stability benefits. The compositions are sterile when first produced, however, when the composition is provided in a multi-use vial or cartridge, an anti-microbial preservative compound or mixture of compounds that is compatible with the other components of the formulation is typically added at sufficient strength to meet regulatory and pharmacopoeial anti-microbial preservative requirements. See U.S. Pharmacopeia Monographs. Insulin lispro injection. USP29-NF24; British Pharmacopeia Monographs 2008 Volume III: Insulin aspart injection; U.S. Pharmacopeia Monographs. Insulin assays; and U.S. Pharmacopeia general chapters. USP29-NF24. Rockville, Md.: U.S. Pharmacopeial Convention; 2005. Antimicrobial effectiveness testing; pp. 2499-2500. Preferred preservatives are aryl acids and phenolic compounds, or mixtures of such compounds. Effective concentrations can be ascertained readily using the methods referenced above. Preservatives commonly used in insulin products include phenol (CAS No. 108-95-2, molecular formula $C_6H_5OH$, molecular weight 94.11), and m-cresol (CAS No. 108-39-4, molecular formula $C_7H_8O$, molecular weight 108.14). Present commercial compositions, for example, contain 3.15 mg/mL m-cresol (HUMALOG® and APIDRA®), 1.72 mg/mL m-cresol and 1.50 mg/mL phenol (NOVOLOG®), and 2.5 mg/mL m-cresol (HUMULIN® R U-500). In an embodiment, the preservative is selected from the group consisting of phenol and m-cresol. Preferably the preservative is m-cresol. In certain embodiments the m-cresol concentration is from about 2.5 to about 3.8 mg/mL. Preferably the concentration of m-cresol is about 3.15 mg/mL.

It is desirable to approximately match the tonicity (i.e., osmolality) of body fluids at the injection site as closely as possible when administering the compositions because solutions that are not approximately isotonic with body fluids can produce a painful stinging sensation when administered. Thus, it is desirable that the compositions be approximately isotonic with body fluids at the sites of injection. If the osmolality of a composition in the absence of a tonicity agent is sufficiently less than the osmolality of the tissue (for blood, about 300 mOsmol/kg; the European Pharmacopeial requirement for osmolality is >240 mOsmol/kg), then a tonicity agent should generally be added to raise the tonicity of the composition to about 300 mOsmol/kg. The osmolality of the composition is determined by the identities and concentrations of other excipients in the composition, including the stabilizing agent(s). Thus, the concentrations of all of the various excipients in a composition must be assessed in order to determine whether a tonicity agent must be added and such assessments and determinations are readily made using standard techniques. See Remington: The Science and Practice of Pharmacy, David B. Troy and Paul Beringer, eds., Lippincott Williams & Wilkins, 2006, pp. 257-259; Remington: Essentials of Pharmaceutics, Linda Ed Felton, Pharmaceutical Press, 2013, pp. 277-300. Typical tonicity agents include glycerol (glycerin), mannitol and sodium chloride. If the addition of a tonicity agent is required, glycerol is preferred. In certain embodiments the concentration of glycerol is from about 1 to about 16 mg/mL. In certain embodiments, the concentration of glycerol is from about 1 to about 2 mg/mL, about 3 to about 4 mg/mL, about 5 to about 6 mg/mL, about 7 to about 8 mg/mL, about 9 to about 10 mg/mL, about 11 to about 12 mg/mL, about 13 to about 14 mg/mL, or about 15 to about 16 mg/mL. In certain embodiments, the concentration of glycerol is about 5, about 12 or about 16 mg/mL.

Citrate, which as noted above is added to contribute to improvements in time action, is also known to also have buffering properties, but if desired an additional buffering compound may be included. Examples of such buffering compounds are phosphate buffers, such as dibasic sodium phosphate, sodium acetate and tris(hydroxymethyl)aminomethane, or TRIS. If an additional buffering compound is necessary, TRIS or phosphate buffers are preferred. The pH for commercial insulin compositions is usually in the range of 7.2 to 7.6, with 7.4±0.1 as a common target pH. The pH of the present invention is typically from about 7.0 to about 7.8 and it is adjusted using physiologically appropriate acids and bases, typically hydrochloric acid 10% and sodium hydroxide 10%. Preferably, the pH is about 7.4.

The route of administration for the compositions of the present invention will typically be by self-administered subcutaneous injection, e.g., by use of a syringe or a pen device, or by continuous subcutaneous insulin infusion therapy with an insulin pump device, though intravenous, intradermal, or intraperitoneal routes may also be used.

As noted above, the present invention also provides an article of manufacture comprising a pharmaceutical composition. In certain embodiments, the article of manufacture is a multi-use vial. In other embodiments, the article of manufacture is a multi-use pre-filled cartridge. In other embodiments, the article of manufacture is a re-usable pen injector. In other embodiments, the article of manufacture is a disposable pen device. In other embodiments, the article of manufacture is a pump device for continuous subcutaneous insulin infusion therapy. In other embodiments, the article of manufacture is a container closure system for use in a pump device for continuous subcutaneous insulin infusion therapy.

In an embodiment, the present invention provides a pharmaceutical composition comprising: an insulin; citrate, in a concentration from about 5 to about 25 mM; treprostinil, in a concentration from about 0.04 to about 20 μg/mL; zinc, in a concentration sufficient to provide at least 2 zinc ions per six molecules of insulin; a preservative; and one or more additional stabilizing agents; and having a pH of about 7.0 to about 7.8 at room temperature.

In certain embodiments, the concentration of zinc ranges from about 0.2 to about 2 mM. In certain embodiments, the zinc concentration is from about 0.2 to about 1 mM. In certain embodiments, the zinc concentration is from about 0.6 to about 0.8 mM. In certain embodiments, the zinc concentration is about 0.6 mM. In certain embodiments, the zinc concentration is about 0.7 mM. In certain embodiments, the zinc concentration is about 0.8 mM. In certain embodiments, the zinc concentration is about 0.9 mM.

In certain embodiments, the one or more additional stabilizing agents are selected from the group consisting of a surfactant, magnesium chloride and sodium chloride.

In certain embodiments, the one or more additional stabilizing agents comprise a surfactant, which is present in a concentration of about 0.003 to about 2% w/v. In certain embodiments, the surfactant is poloxamer 188. In certain embodiments, the concentration of poloxamer 188 is from about 0.06 to about 0.12% w/v. In certain embodiments, the concentration of poloxamer 188 is about 0.06% w/v. In certain embodiments, the concentration of poloxamer 188 is about 0.09% w/v. In certain embodiments, the concentration of poloxamer 188 is about 0.12% w/v.

In certain embodiments, the one or more additional stabilizing agents comprise magnesium chloride, which is present in a concentration resulting in a molar ratio of magnesium chloride to citrate from about 1:2 to about 1:10. In certain embodiments, the ratio of magnesium ranges from about 1:1 to about 1:5. In certain embodiments, the molar ratio of magnesium chloride to citrate is from about 1:3 to about 1:5. In certain embodiments, the concentration of magnesium ranges from about 1 about 15 mM. In certain embodiments, the concentration of magnesium ranges from about 1 about 5 mM, about 5 to about 10 mM or about 10 to about 15 mM. In certain embodiments, the concentration of magnesium is about 2.5, about 5, about 7.5 or about 10 mM.

In certain embodiments, the one or more additional stabilizing agents comprise sodium chloride, which is present in a concentration of about 10 to about 40 mM. In certain embodiments, the sodium chloride concentration is from about 15 to about 25 mM. In certain embodiments, the total chloride concentration is not more than about 50 mM. In certain embodiments, the total chloride concentration ranges from about 10 to about 50 mM. In certain embodiments, the total chloride concentration ranges from about 13 to about 45 mM. In certain embodiments, the total chloride concentration ranges from about 20 to about 25 mM. In certain embodiments, the total chloride concentration ranges from about 15 to about 35 mM. In certain embodiments, the total chloride concentration ranges from about 20 to about 25 mM. In certain embodiments, the total chloride concentration is about 15 mM, about 16 mM, about 17 mM, about 18 mM, about 19 mM, about 20 mM, about 21 mM, about 22 mM, about 23 mM, about 24 mM or about 25 mM.

In certain embodiments, the insulin concentration is from about 100 to about 500 U/mL. In certain embodiments, the insulin concentration is from about 100 to about 300 U/mL. In certain embodiments, the insulin concentration is either about 100 U/mL or about 200 U/mL. In certain embodiments, the insulin is insulin lispro.

In certain embodiments, the concentration of citrate is from about 10 to about 25 mM. In certain embodiments, the concentration of citrate is about 15 mM.

In certain embodiments, the composition comprises treprostinil in a concentration from about 0.04 to about 20 μg/mL. In certain embodiments, the concentration of treprostinil is from about 0.04 to about 10 μg/mL. In certain embodiments, the concentration of treprostinil is from about 0.5 to about 2 µg/mL. In certain embodiments, the concentration of treprostinil is about 1 µg/mL.

In certain embodiments, the preservative is m-cresol. In certain embodiments, the concentration of m-cresol is from about 2.5 to about 3.8 mg/mL. In certain embodiments, the concentration of m-cresol is about 3.15 mg/mL.

In certain embodiments, the composition further comprises a tonicity agent. In certain embodiments, the tonicity agent is glycerol. In certain embodiments, the concentration of glycerol is from about 1 to about 15 mg/mL. In certain embodiments, the concentration of glycerol is from about 1 to about 2 mg/mL.

In certain embodiments, the pharmaceutical composition provides for an uptake of insulin into the blood, onset of action and/or duration of action that is at least 20% more rapid than for compositions which contain the same insulin but which do not contain citrate or treprostinil, when measured by one or more pharmacokinetic or pharmacodynamic parameters relevant to time action, such as: time to maximum insulin concentration (Tmax); time to reach one half of the maximum insulin concentration (early ½ Tmax); time to reach one half of the maximum insulin concentration during the declining phase of the concentration-over-time curve (late 12 Tmax); time between early and late ½ Tmax (Tmax spread); percentage of total insulin dose absorbed at different times based on fractional area under the insulin concentration curve (e.g., $AUC_{0-30min}$, $AUC_{0-60min}$, $AUC_{0-120\ min}$, $AUC_{0-180min}$); time to reach one half of the total insulin concentration (T50); time to reach maximal glucose infusion rate (GIRmax), time to reach one half of the maximum glucose infusion rate (early ½ GIRmax); time to reach one half of the maximum glucose infusion rate during the declining phase of the concentration-over-time curve (late ½ GIRmax); percentage of total glucose infused at different times based on fractional area under the GIR curve (e.g., $GIR_{0-30min}$, $GIR_{0-60min}$, $GIR_{0-120\ min}$, $GIR_{0-180min}$).

In certain embodiments, the pharmaceutical composition provides for an uptake of insulin into the blood, onset of action and/or duration of action that is at least 30%, at least 40% or at least 50% more rapid than for compositions which contain the same insulin but which do not contain citrate or treprostinil, when measured by one or more pharmacokinetic or pharmacodynamic parameters described above.

In certain embodiments, the pharmaceutical composition provides for an uptake of insulin into the blood, onset of action and/or duration of action that is between about 20 to about 50%, between about 20 to about 30%, between about 30 to about 40% or between about 40 to about 50% more rapid than for compositions which contain the same insulin but which do not contain citrate or treprostinil, when measured by one or more pharmacokinetic or pharmacodynamic parameters described above.

In certain embodiments, the pharmaceutical composition does not include any additional chelating agent, such as EDTA, any additional vasodilatory agent, such as nitroglycerin, and/or any oligosaccharides.

In certain embodiments, the pharmaceutical composition is stable to allow for storage of at least 24 months at 2-8° C. and up to 28 days in-use at temperatures of up to 30° C. for vials or cartridges in re-usable pen injectors. In certain embodiments, the pharmaceutical composition is stable to allow for storage of at least 36 months at 2-8° C. and up to 28 days in-use at temperatures of up to 30° C. for vials or cartridges in re-usable pen injectors.

In certain embodiments, the composition is stable to allow for use in a pump device for continuous subcutaneous insulin infusion therapy for up to 7 days.

Additional embodiments of the present invention include those described below:

1. A pharmaceutical composition comprising: an insulin; citrate; and treprostinil.

2. The pharmaceutical composition of the above-described embodiment, wherein the insulin is selected from the group consisting of human insulin, insulin lispro, insulin aspart or insulin glulisine.

3. The pharmaceutical composition of any of the above-described embodiments, wherein the insulin is insulin lispro.

4. The pharmaceutical composition of any of the above-described embodiments, wherein the insulin concentration is from about 100 to about 500 U/mL.

5. The pharmaceutical composition of any of the above-described embodiments, wherein the insulin concentration is from about 100 to about 300 U/mL.

6. The pharmaceutical composition of any of the above-described embodiments, wherein the insulin concentration is from about 100 to about 200 U/mL.

7. The pharmaceutical composition of any of the above-described embodiments, wherein the insulin concentration is about 100 U/mL.

8. The pharmaceutical composition of any of the above-described embodiments, wherein the insulin concentration is about 200 U/mL.

9. The pharmaceutical composition of any of the above-described embodiments, wherein the concentration of citrate is from about 5 to about 25 mM.

10. The pharmaceutical composition of any of the above-described embodiments, wherein the concentration of citrate is from about 15 to about 25 mM.

11. The pharmaceutical composition of any of the above-described embodiments, wherein the concentration of citrate is from about 15 to about 20 mM.

12. The pharmaceutical composition of any of the above-described embodiments, wherein the concentration of citrate is about 5, about 10, about 12, about 15, about 18, about 20 or about 25 mM.

13. The pharmaceutical composition of any of the above-described embodiments, wherein the concentration of citrate is about 15 mM 14. The pharmaceutical composition of any of the above-described embodiments, wherein the concentration of treprostinil is from about 0.04 to about 20 µg/mL.

15. The pharmaceutical composition of any of the above-described embodiments, wherein the concentration of treprostinil is from about 0.04 to about 10 µg/mL.

16. The pharmaceutical composition of any of the above-described embodiments, wherein the concentration of treprostinil is from about 0.5 to about 10 µg/mL.

17. The pharmaceutical composition of any of the above-described embodiments, wherein the concentration of treprostinil is from about 0.5 to about 2 µg/mL.

18. The pharmaceutical composition of any of the above-described embodiments, wherein the concentration of treprostinil is about 0.5, about 0.6, about 1, about 2, about 2.3, about 9.3 or about 10 µg/mL.

19. The pharmaceutical composition of any of the above-described embodiments, wherein the concentration of treprostinil is about 1 µg/mL.

20. The pharmaceutical composition of any of the above-described embodiments, wherein the composition further comprises zinc.

21. The pharmaceutical composition of any of the above-described embodiments, wherein the concentration of zinc is from about 0.2 to about 2 mM.

22. The pharmaceutical composition of any of the above-described embodiments, wherein the concentration of zinc is from about 0.3 to about 1.7 mM.

23. The pharmaceutical composition of any of the above-described embodiments, wherein the concentration of zinc is from about 0.7 to about 1.7 mM.

24. The pharmaceutical composition of any of the above-described embodiments, wherein the concentration of zinc is from about 0.3 to about 1 mM.

25. The pharmaceutical composition of any of the above-described embodiments, wherein the concentration of zinc is from about 0.4 to about 0.8 mM.

26. The pharmaceutical composition of any of the above-described embodiments, wherein the concentration of zinc is about 0.3, about 0.4, about 0.5, about 0.6, about 0.7 about 0.8, about 0.9 mM, about 1.25 or about 1.7 mM.

27. The pharmaceutical composition of any of the above-described embodiments, wherein the concentration of zinc is about 0.6 mM.

28. The pharmaceutical composition of any of the above-described embodiments, wherein the concentration of zinc is about 0.7 mM.

29. The pharmaceutical composition of any of the above-described embodiments, wherein the concentration of zinc is about 0.8 mM.

30. The pharmaceutical composition of any of the above-described embodiments, wherein the concentration of zinc is about 0.9 mM.

31. The pharmaceutical composition of any of the above-described embodiments, further comprising magnesium.

32. The pharmaceutical composition of any of the above-described embodiments comprising magnesium which is present in a concentration resulting in a molar ratio of magnesium to citrate from about 1:2 to about 1:10.

33. The pharmaceutical composition of any of the above-described embodiments comprising magnesium which is present in a concentration resulting in a molar ratio of magnesium to citrate from about 1:1 to about 1:5.

34. The pharmaceutical composition of the above-described embodiments, wherein the molar ratio of magnesium to citrate is from about 1:3 to about 1:5.

35. The pharmaceutical composition of any of the above-described embodiments, comprising magnesium in a concentration from about 1 to about 15 mM.

36. The pharmaceutical composition of any of the above-described embodiments, comprising magnesium in a concentration from about 2.5 to about 10 mM.

37. The pharmaceutical composition of any of the above-described embodiments, comprising magnesium in a concentration from about 5 to about 10 mM.

38. The pharmaceutical composition of any of the above-described embodiments, comprising magnesium in a concentration from about 2.5 to about 7.5 mM.

39. The pharmaceutical composition of any of the above-described embodiments, comprising magnesium in a concentration of about 2.5, about 5, about 7.5 or about 10 mM.

40. The pharmaceutical composition of any of the above-described embodiments comprising magnesium wherein the magnesium is provided as magnesium chloride.

41. The pharmaceutical composition of the above-described embodiments, further comprising sodium chloride.

42. The pharmaceutical composition of any of the above-described embodiments, wherein the composition comprises sodium chloride in a concentration ranging from about 1 to about 50 mM.

43. The pharmaceutical composition of any of the above-described embodiments, wherein the composition comprises sodium chloride in a concentration ranging from about 10 to about 40 mM.

44. The pharmaceutical composition of any of the above-described embodiments, wherein the composition comprises sodium chloride in a concentration ranging from about 15 to about 25 mM.

45. The pharmaceutical composition of any of the above-described embodiments, wherein the composition comprises sodium chloride in a concentration ranging from about 1 to about 20 mM.

46. The pharmaceutical composition of any of the above-described embodiments, wherein the composition comprises sodium chloride in a concentration of about 1, about 2, about 3, about 4, about 5, about 6, about 7, about 8, about 9, about 10, about 11, about 12, about 13, about 14, about 15, about 16, about 17, about 18, about 19 or about 20 mM.

47. The pharmaceutical composition of any of the above-described embodiments, wherein the total chloride concentration is from about 1 to about 100 mM.

48. The pharmaceutical composition of any of the above-described embodiments, wherein the total chloride concentration is from about 10 to about 100 mM.

49. The pharmaceutical composition of any of the above-described embodiments, wherein the total chloride concentration ranges from about 10 to about 50 mM.

50. The pharmaceutical composition of any of the above-described embodiments, wherein the total chloride concentration ranges from about 13 to about 45 mM.

51. The pharmaceutical composition of any of the above-described embodiments, wherein the total chloride concentration ranges from about 16 to about 35 mM.

52. The pharmaceutical composition of any of the above-described embodiments, wherein the total chloride concentration ranges from about 20 to about 25 mM.

53. In certain embodiments, the total chloride concentration is about 15 mM, about 16 mM, about 17 mM, about 18 mM, about 19 mM, about 20 mM, about 21 mM, about 22 mM, about 23 mM, about 24 mM or about 25 mM.

54. The pharmaceutical composition of any of the above-described embodiments, wherein the composition further comprises a surfactant.

55. The pharmaceutical composition of any of the above-described embodiments, wherein the composition further comprises poloxamer 188.

56. The pharmaceutical composition of any of the above-described embodiments, comprising poloxamer 188 in a concentration of about 0.003 to about 2% w/v.

57. The pharmaceutical composition of any of the above-described embodiments, comprising poloxamer 188 in a concentration of about 0.003 to about 0.3% w/v.

58. The pharmaceutical composition of any of the above-described embodiments, comprising poloxamer 188 in a concentration of about 0.01 to about 0.2% w/v.

59. The pharmaceutical composition of any of the above-described embodiments, comprising poloxamer 188 in a concentration of about 0.06 to about 0.12 w/v.

60. The pharmaceutical composition of any of the above-described embodiments, wherein the composition further comprises a preservative.

61. The pharmaceutical composition of any of the above-described embodiments, comprising a preservative which is selected from the group consisting of m-cresol and phenol.

62. The pharmaceutical composition of any of the above-described embodiments, comprising a preservative which is m-cresol.

63. The pharmaceutical composition of any of the above-described embodiments, comprising m-cresol in a concentration from about 2.5 to about 3.8 mg/mL.

64. The pharmaceutical composition of any of the above-described embodiments, comprising m-cresol in a concentration of about 3.15 mg/mL.

65. The pharmaceutical composition of the above-described embodiments, further comprising a tonicity agent.

66. The pharmaceutical composition of the above-described embodiments, comprising a tonicity agent which is glycerol.

67. The pharmaceutical composition of the above-described embodiments, comprising glycerol in a concentration from about 1 to about 20 mg/mL.

68. The pharmaceutical composition of the above-described embodiments, comprising glycerol in a concentration from about 1 to about 15 mg/mL.

69. The pharmaceutical composition of the above-described embodiments, comprising glycerol in a concentration from about 1 to about 2 mg/mL, about 3 to about 4 mg/mL, about 5 to about 6 mg/mL, about 7 to about 8 mg/mL, about 9 to about 10 mg/mL, about 11 to about 12 mg/mL, about 13 to about 14 mg/mL or about 15 to about 16 mg/mL.

70. The pharmaceutical composition of the above-described embodiments, comprising glycerol in a concentration of about 5, about 12 or about 16 mg/mL.

71. The pharmaceutical composition of the above-described embodiments, comprising glycerol in a concentration of about 12 mg/mL.

The invention is further illustrated by the following examples, which are not to be construed as limiting.

EXAMPLES

Pharmacokinetic and Pharmacodynamic Studies
Insulin Lispro Formulated with 0.5 μg/ml Treprostinil and/or 15 mM Sodium Citrate Diabetic (Alloxan induced), castrated, male Yucatan miniature swine (average age 23 months, average body weight 45 kgs) with previously fitted vascular access ports are used under the supervision of staff and veterinarians. The diabetic animals are housed individually and have access to fresh water at all times. They are fed two meals per day of a standard diet and receive appropriate maintenance basal and prandial insulin twice per day to manage their diabetic condition.

Test articles (Compositions A, B and C in the table below) are formulated by adding the indicated amounts of citrate and/or treprostinil to a vial of Humalog®. The necessary quantity of treprostinil is withdrawn from a vial of 1 mg/mL Remodulin®. Each mL of Remodulin® also contains 3 mg m-cresol, 6.3 mg sodium citrate and 5.3 mg sodium chloride, so the addition of treprostinil to the test compositions also results in the addition of small amounts of these excipients, as well as a slight dilution of the Humalog® excipients. Such small quantities are not believed to affect the properties of the compositions, however, and are thus not reflected in Table 1 below.

TABLE 1

| Name | Formulation |
| --- | --- |
| Composition A | 100 Units/ml insulin lispro<br>0.5 μg/ml treprostinil<br>1.88 mg/ml phosphate |

TABLE 1-continued

| Name | Formulation |
| --- | --- |
| Composition B | 3.15 mg/ml m-cresol<br>16 mg/ml glycerol<br>0.3 mM Zn<br>pH 7.4<br>98 Units/ml insulin lispro<br>15 mM sodium citrate<br>1.88 mg/ml phosphate<br>3.15 mg/ml m-cresol<br>16 mg/ml glycerol<br>0.3 mM Zn<br>pH 7.4 |
| Composition C | 98 Units/ml insulin lispro<br>15 mM sodium citrate<br>0.5 μg/ml treprostinil<br>1.88 mg/ml phosphate<br>3.15 mg/ml m-cresol<br>16 mg/ml glycerol<br>0.3 mM Zn<br>pH 7.4 |
| Humalog ® | 100 U/mL insulin lispro<br>1.88 mg/ml phosphate<br>16 mg/mL glycerol<br>3.15 mg/mL meta-cresol<br>0.3 mM zinc<br>pH 7.4 |

The day prior to study, animals are fed half their daily ration and receive 0.2 U/kg Humalog® Mix 75/25 Insulin at their morning maintenance administration. All study animals are food-fasted overnight and do not receive their evening insulin or meal prior to drug administration on study day.

On the morning of study, all animals are placed into slings for restraint and have their vascular access ports accessed (equipped for blood sampling) and checked for patency. The animals are randomly placed into treatment groups.

Study is a full crossover design with n=20. One animal is withheld from two of the four parts due to port non-patency, so compositions A and C are n=19 while composition B and Humalog® are n=20.

After two baseline blood samples are collected (−30 and −20 min), the animals are returned to their pens and are fed ~300 g. Twenty minutes after the presentation of the fully consumed meal, the animals are injected with test article subcutaneously in the flank (0 min) with a Terumo insulin syringe (0.3 or 0.5 ml with ½" needle). All study animals have access to clean, fresh water throughout the remaining blood collection period.

Serial blood samples (2.0 mL each) are collected from each animal at the following time points: −30, −20 (then immediately fed), 0 (just before dose), 5, 10, 15, 30, 45, 60, 75, 90, 105, 120, 150, 180, 240, and 360 minutes following the SC dosing.

Blood samples (anticoagulant: none [serum]) are maintained at ambient temperature for at least 30 minutes but no more than 2 hours to allow for clotting. Serum is then separated by centrifugation and divided into two aliquots and stored frozen at approximately −70° C.

Serum glucose concentrations are determined using an automated AU480 Clinical Chemistry Analyzer (Beckman Coulter, Inc., Brea, Calif.). Aliquot for PK is shipped to EMD Millipore Corp., St. Charles, Mo. on dry ice by a next day shipping service and included a detailed sample manifest.

Serum glucose data are represented in Table 2 below as mean (mg/dL)+/−standard error of the mean (SEM) unless otherwise specified.

TABLE 2

| Time | Humalog ® | | Composition A | | Composition B | | Composition C | |
|---|---|---|---|---|---|---|---|---|
| (min) | AVG | SEM | AVG | SEM | AVG | SEM | AVG | SEM |
| −30 | 290.2 | 8.6 | 286.8 | 9.0 | 289.2 | 8.1 | 283.2 | 8.4 |
| −20 | 297.6 | 8.5 | 299.2 | 10.2 | 297.6 | 9.0 | 297.5 | 7.5 |
| 0 | 311.3 | 8.6 | 311.0 | 10.7 | 312.2 | 9.5 | 309.6 | 7.4 |
| 5 | 318.1 | 8.9 | 316.8 | 10.0 | 319.0 | 9.6 | 314.9 | 8.1 |
| 10 | 318.9 | 8.6 | 315.3 | 11.4 | 305.2 | 11.7 | 295.7 | 10.3 |
| 15 | 312.3 | 9.2 | 297.6 | 13.5 | 276.6 | 12.8 | 265.1 | 11.6 |
| 30 | 297.1 | 9.8 | 251.9 | 18.6 | 220.3 | 16.2 | 205.5 | 17.0 |
| 45 | 288.3 | 12.0 | 233.1 | 16.7 | 204.5 | 18.5 | 209.8 | 17.1 |
| 60 | 244.1 | 14.7 | 187.9 | 17.5 | 178.5 | 18.6 | 159.2 | 20.0 |
| 75 | 231.5 | 15.3 | 166.6 | 18.2 | 169.0 | 20.4 | 146.3 | 20.4 |
| 90 | 204.6 | 15.6 | 145.7 | 18.5 | 157.7 | 21.4 | 133.2 | 21.1 |
| 105 | 181.9 | 15.9 | 127.0 | 18.1 | 144.7 | 21.4 | 118.7 | 18.9 |
| 120 | 153.3 | 16.2 | 111.4 | 17.3 | 128.2 | 21.1 | 111.7 | 18.5 |
| 150 | 120.2 | 16.8 | 86.4 | 15.8 | 115.7 | 20.0 | 102.9 | 15.9 |
| 180 | 101.5 | 16.5 | 76.4 | 14.5 | 106.3 | 18.2 | 97.0 | 13.2 |
| 240 | 82.8 | 12.2 | 92.3 | 14.2 | 100.7 | 13.3 | 98.6 | 12.3 |
| 360 | 90.3 | 14.4 | 130.5 | 18.2 | 111.8 | 17.2 | 126.3 | 17.0 |

Serum insulin concentrations for PK analysis are measured using a total insulin RIA. Lower and upper limits of quantitation for the assay are 20 pM and 5000 pM, respectively. Values below the lower limit of quantitation are assumed to be 20 pM. Non-compartmental pharmacokinetic analyses are performed using Phoenix WinNonlin v6.3. PK parameters derived from serum insulin concentrations are provided in Table 3 below.

TABLE 3

| Composition | | Tmax (min) | Early ½ Max (min) | Late ½ Max (min) | Tmax Spread (min) | T50 (min) |
|---|---|---|---|---|---|---|
| Humalog ® | Mean (SE) | 71.3 (7.3) | 29.6 (4.1) | 175 (14) | 145 (14) | 127 (6) |
| A | Mean (SE) | 74.2 (7.6) | 24.1 (3.8) | 146 (12) | 122 (13) | 102 (5) |
| B | Mean (SE) | 55.5 (7.8) | 16.5 (4.9) | 130 (12) | 113 (14) | 100 (6) |
| C | Mean (SE) | 42.1 (6.6) | 15.9 (3.9) | 98.5 (13.4) | 82.6 (13.6) | 83.4 (5.7) |

This study supports that compositions of the present invention have improved pharmacokinetic and/or pharmacodynamic time action.

Insulin Lispro Formulated with 10 mM Citrate and/or 10 mg/mL Treprostinil

A study on compositions comprising varying concentrations of citrate and/or μg/mL treprostinil is performed in diabetic (Alloxan induced), castrated, male Yucatan miniature swine (average age 24 months, average body weight 43 kgs) following generally the procedures described above.

Test articles (Compositions D-H in the table below) are formulated by adding the indicated amounts of citrate and/or treprostinil to a vial of Humalog®. As with the study described above, the necessary quantity of treprostinil is withdrawn from a vial of 1 mg/mL Remodulin®, so the addition of treprostinil to the test compositions also results in the addition of small quantities of m-cresol, sodium citrate and sodium chloride, as well as a slight dilution of the Humalog® excipients. Such small quantities are not believed to affect the properties of the compositions, however, and are thus not reflected in Table 4 below.

TABLE 4

| Name | Formulation Composition |
|---|---|
| Composition D | 99.7 U/ml insulin lispro |
| | 5 mM citrate |
| | 0.3 mM zinc |
| | 3.15 mg/mL meta-cresol |
| | 16 mg/ml glycerine |
| | 1.88 mg/ml phosphate |
| Composition E | 99.2 U/ml insulin lispro |
| | 10 mM citrate |
| | 0.3 mM zinc |
| | 3.15 mg/mL meta-cresol |
| | 16 mg/ml glycerine |
| | 1.88 mg/ml phosphate |
| Composition F | 99.2 U/ml insulin lispro |
| | 10 μg/ml treprostinil |
| | 0.3 mM zinc |
| | 3.15 mg/mL meta-cresol |
| | 16 mg/ml glycerine |
| | 1.88 mg/ml phosphate |
| Composition G | 100.2 U/ml Insulin lispro |
| | 5 mM citrate |
| | 10 μg/ml treprostinil |
| | 0.3 mM zinc |
| | 3.15 mg/mL meta-cresol |
| | 16 mg/ml glycerine |
| | 1.88 mg/ml phosphate |
| Composition H | 99.6 U/ml Insulin lispro |
| | 10 mM citrate |
| | 10 μg/ml treprostinil |
| | 0.3 mM zinc |
| | 3.15 mg/mL meta-cresol |

TABLE 4-continued

| Name | Formulation Composition |
|---|---|
| | 16 mg/ml glycerine |
| | 1.88 mg/ml phosphate |
| Humalog ® | 100 U/mL KPB |
| | 1.88 mg/mL dibasic sodium phosphate |
| | 16 mg/mL glycerol |
| | 3.15 mg/mL meta-cresol |
| | 0.3 mM zinc |
| | pH 7.4 |

Study is designed as a 19 pig full cross over design in which each pig is studied on each test article. A few animals do not participate on study due to port non-patency therefore formulations D and E are n=18 while formulations F-H are n=19 and Humalog® n=17.

Serum glucose data are represented in Table 5 below as mean (mg/dL)+/−SEM unless otherwise specified.

TABLE 5

| Time (min) | Humalog® AVG | Humalog® SEM | Composition D AVG | Composition D SEM | Composition E AVG | Composition E SEM | Composition F AVG | Composition F SEM | Composition G AVG | Composition G SEM | Composition H AVG | Composition H SEM |
|---|---|---|---|---|---|---|---|---|---|---|---|---|
| −30 | 340.5 | 8.2 | 340.2 | 8.9 | 321.2 | 7.3 | 335.2 | 8.5 | 337.4 | 7.5 | 331.8 | 10.1 |
| −20 | 344.4 | 8.0 | 341.3 | 9.2 | 326.2 | 7.8 | 339.8 | 7.7 | 344.6 | 6.7 | 338.6 | 11.0 |
| 0 | 362.6 | 7.7 | 353.2 | 10.3 | 339.4 | 9.5 | 357.8 | 7.9 | 354.7 | 7.7 | 349.1 | 11.4 |
| 5 | 377.6 | 7.9 | 370.6 | 9.8 | 349.5 | 11.9 | 367.9 | 8.0 | 369.1 | 8.5 | 368.2 | 12.4 |
| 10 | 376.7 | 8.4 | 360.7 | 9.3 | 329.6 | 12.0 | 361.0 | 11.1 | 361.9 | 9.0 | 345.6 | 13.4 |
| 15 | 372.4 | 10.1 | 341.7 | 13.2 | 307.6 | 13.7 | 348.1 | 12.3 | 342.6 | 9.1 | 321.6 | 14.6 |
| 30 | 339.8 | 17.9 | 292.2 | 17.3 | 256.6 | 18.5 | 304.1 | 14.7 | 299.0 | 12.9 | 276.4 | 20.6 |
| 45 | 301.5 | 21.8 | 251.1 | 21.0 | 230.9 | 20.9 | 263.1 | 18.0 | 254.6 | 16.0 | 237.3 | 24.2 |
| 60 | 272.4 | 25.7 | 224.2 | 21.3 | 207.3 | 20.1 | 230.9 | 21.6 | 230.3 | 18.3 | 208.8 | 26.4 |
| 75 | 253.0 | 26.7 | 202.3 | 22.6 | 178.2 | 19.3 | 197.2 | 22.8 | 196.9 | 20.3 | 168.5 | 25.2 |
| 90 | 220.2 | 28.3 | 186.1 | 23.0 | 164.6 | 20.5 | 173.4 | 23.5 | 173.6 | 21.4 | 153.8 | 26.2 |
| 105 | 195.6 | 27.6 | 148.2 | 20.0 | 144.3 | 19.6 | 148.6 | 23.1 | 147.6 | 20.9 | 131.8 | 24.2 |
| 120 | 184.4 | 27.5 | 133.3 | 19.1 | 129.9 | 18.2 | 130.0 | 22.6 | 124.9 | 20.4 | 115.4 | 23.0 |
| 150 | 158.2 | 24.8 | 114.1 | 17.7 | 104.6 | 18.5 | 101.4 | 18.6 | 98.8 | 16.8 | 90.1 | 18.3 |
| 180 | 134.3 | 22.0 | 102.7 | 16.5 | 86.1 | 15.8 | 90.8 | 17.5 | 92.2 | 14.6 | 76.8 | 15.9 |
| 240 | 122.4 | 19.7 | 93.7 | 16.4 | 75.2 | 12.4 | 93.5 | 15.0 | 91.1 | 17.5 | 74.4 | 11.7 |
| 360 | 118.4 | 17.1 | 104.0 | 15.8 | 90.7 | 15.1 | 113.9 | 13.7 | 113.7 | 14.1 | 105.1 | 11.1 |

Serum insulin concentrations and PK parameters for Humalog® control and compositions E, F and H are generated and analyzed generally as described above, and PK results are provided in table 6 below.

TABLE 6

| Composition | Tmax (min) | Early ½ Max (min) | Late ½ Max (min) | Spread (min) | T50 (min) |
|---|---|---|---|---|---|
| Humalog® | Mean (SE) 69.7 (12.5) | 17.8 (4.1) | 155 (16) | 138 (16) | 113 (7) |
| E | Mean (SE) 53.8 (10.3) | 6.46 (0.55) | 151 (15) | 144 (15) | 104 (5) |
| F | Mean (SE) 54.2 (7.29) | 23.1 (4.8) | 110 (11) | 87.1 (10.8) | 89.4 (5.7) |
| H | Mean (SE) 39.5 (4.95) | 9.85 (1.77) | 109 (11) | 99.6 (11.5) | 90.7 (5.5) |

This study supports that compositions of the present invention have improved pharmacokinetic and/or pharmacodynamic time action.

Insulin Lispro Formulated with 15 mM Citrate and 0.6-9.3 µg/mL Treprostinil

A study on compositions comprising 15 mM citrate and/or varying concentrations of treprostinil is performed in diabetic (Alloxan induced), castrated, male Yucatan miniature swine (average age 25 months, average body weight 43 kgs) following generally the procedures described above.

Test articles (Compositions I-M in the table below) are formulated by adding the indicated amounts of citrate and/or treprostinil, as well as MgCl$_2$ and/or NaCl in the compositions specified below, to a vial of Humalog®. As with the study described above, the necessary quantity of treprostinil is withdrawn from a vial of 1 mg/mL Remodulin®, so the addition of treprostinil to the test compositions also results in the addition of small quantities of m-cresol, sodium citrate and sodium chloride, as well as a slight dilution of the Humalog® excipients. Such small quantities are not believed to affect the properties of the compositions, however, and are thus not reflected in Table 7 below.

TABLE 7

| Name | Formulation Composition |
|---|---|
| Composition I | 99.1 U/ml Insulin lispro<br>15 mM citrate<br>5 mM MgCl2<br>15 mM NaCl<br>0.3 mM zinc<br>3.15 mg/mL meta-cresol<br>1.88 mg/mL dibasic sodium phosphate<br>16 mg/ml glycerin, |
| Composition J | 99.8 U/ml Insulin lispro<br>9.30 µg/ml treprostinil<br>0.3 mM zinc<br>3.15 mg/mL meta-cresol<br>1.88 mg/mL dibasic sodium phosphate<br>16 mg/ml glycerin |
| Composition K | 99.6 U/ml Insulin lispro<br>15 mM citrate<br>5 mM MgCl2<br>15 mM NaCl<br>0.60 µg/ml treprostinil<br>0.3 mM zinc<br>3.15 mg/mL meta-cresol<br>1.88 mg/mL dibasic sodium phosphate<br>16 mg/ml glycerin |
| Composition L | 100.4 U/ml Insulin lispro<br>15 mM citrate<br>5 mM MgCl2<br>15 mM NaCl<br>2.30 µg/ml treprostinil<br>0.3 mM zinc<br>3.15 mg/mL meta-cresol<br>1.88 mg/mL dibasic sodium phosphate<br>16 mg/ml glycerin |
| Composition M | 100.3 U/ml Insulin lispro<br>15 mM citrate<br>5 mM MgCl2<br>15 mM NaCl<br>9.30 µg/ml treprostinil |

TABLE 7-continued

| Name | Formulation Composition |
| --- | --- |
| Humalog ® | 0.3 mM zinc<br>3.15 mg/mL meta-cresol<br>1.88 mg/mL dibasic sodium phosphate<br>16 mg/ml glycerin<br>100 U/mL KPB<br>1.88 mg/mL dibasic sodium phosphate<br>16 mg/mL glycerol<br>3.15 mg/mL meta-cresol<br>0.3 mM zinc<br>pH 7.4 |

Study is designed as a 17 pig full cross over design in which each pig is studied on each test article. Some animals do not participate on study due to port non-patency or low baseline glucose. Data for Humalog® is n=17, Composition I is n=17, Composition J is n=16, Composition K is n=15, Composition L is n=16 and Composition M is n=16.

Serum glucose data are represented in Table 8 below as mean (mg/dL)+/−SEM unless otherwise specified.

TABLE 8

| Time (min) | Humalog ® AVG | SEM | Composition I AVG | SEM | Composition J AVG | SEM | Composition K AVG | SEM | Composition L AVG | SEM | Composition M AVG | SEM |
| --- | --- | --- | --- | --- | --- | --- | --- | --- | --- | --- | --- | --- |
| −30 | 302.5 | 7.0 | 324.0 | 7.2 | 322.4 | 11.0 | 319.6 | 10.4 | 337.6 | 13.6 | 321.6 | 7.9 |
| −20 | 310.7 | 7.8 | 330.7 | 7.6 | 330.3 | 10.3 | 324.5 | 12.1 | 345.3 | 13.8 | 325.4 | 7.6 |
| 0 | 321.9 | 8.6 | 338.5 | 9.3 | 340.1 | 11.9 | 335.9 | 11.7 | 357.0 | 15.7 | 332.2 | 8.9 |
| 5 | 335.6 | 9.4 | 353.8 | 9.2 | 356.9 | 12.6 | 346.2 | 12.0 | 371.2 | 15.7 | 346.4 | 9.2 |
| 10 | 340.3 | 9.8 | 347.0 | 9.6 | 356.7 | 11.7 | 337.7 | 14.4 | 365.6 | 16.5 | 339.2 | 11.8 |
| 15 | 326.6 | 9.7 | 315.6 | 10.9 | 340.1 | 10.7 | 306.5 | 13.7 | 339.0 | 17.3 | 302.4 | 13.4 |
| 30 | 276.6 | 17.6 | 264.1 | 17.9 | 271.9 | 15.5 | 240.0 | 15.4 | 274.7 | 23.1 | 244.0 | 20.6 |
| 45 | 241.2 | 22.9 | 220.2 | 20.2 | 237.5 | 14.4 | 197.9 | 20.8 | 226.7 | 26.8 | 195.1 | 22.6 |
| 60 | 202.1 | 26.0 | 186.9 | 21.5 | 192.9 | 17.8 | 160.3 | 21.4 | 195.9 | 27.5 | 157.9 | 23.6 |
| 75 | 182.5 | 27.2 | 159.9 | 22.1 | 155.7 | 19.8 | 140.9 | 21.2 | 171.4 | 28.1 | 136.8 | 22.7 |
| 90 | 158.0 | 27.4 | 141.2 | 23.9 | 133.0 | 19.2 | 119.5 | 21.5 | 153.2 | 27.4 | 122.0 | 21.1 |
| 105 | 142.7 | 25.2 | 127.1 | 23.2 | 118.0 | 19.8 | 105.3 | 19.8 | 132.6 | 25.6 | 115.9 | 20.3 |
| 120 | 122.8 | 23.6 | 115.8 | 21.6 | 98.7 | 18.5 | 94.5 | 17.3 | 121.8 | 24.8 | 99.3 | 18.6 |
| 150 | 107.9 | 21.6 | 101.3 | 18.2 | 72.5 | 15.7 | 82.8 | 14.3 | 110.3 | 21.7 | 87.6 | 17.1 |
| 180 | 90.4 | 17.1 | 98.6 | 18.2 | 66.4 | 11.9 | 79.2 | 11.2 | 101.8 | 20.4 | 88.2 | 15.4 |
| 240 | 83.4 | 14.5 | 96.5 | 16.8 | 72.0 | 8.0 | 97.1 | 11.8 | 111.2 | 22.2 | 98.3 | 14.3 |
| 360 | 86.0 | 18.6 | 96.1 | 13.3 | 122.2 | 16.5 | 149.5 | 19.8 | 156.8 | 21.2 | 125.4 | 20.4 |

Serum insulin concentrations and PK parameters are generated and analyzed generally as described above, and PK results are provided in table 9 below.

TABLE 9

| Composition | | Tmax (min) | Early ½ Max (min) | Late ½ Max (min) | Spread (min) | T50 (min) |
| --- | --- | --- | --- | --- | --- | --- |
| Humalog ® | Mean (SE) | 60.0 (7.6) | 22.9 (5.8) | 152 (17) | 129 (18) | 107 (7) |
| I | Mean (SE) | 57.1 (9.5) | 16.0 (3.5) | 144 (16) | 128 (17) | 102 (5) |
| J | Mean (SE) | 55.3 (5.3) | 13.7 (1.5) | 139 (9) | 125 (9) | 96.8 (4.6) |
| K | Mean (SE) | 55.0 (6.2) | 15.8 (2.2) | 136 (10) | 120 (11) | 91.1 (4.8) |
| L | Mean (SE) | 50.0 (7.2) | 13.2 (2.1) | 121 (10) | 108 (10) | 90.7 (6.6) |
| M | Mean (SE) | 52.5 (7.4) | 11.7 (1.5) | 139 (18) | 127 (18) | 99.0 (7.4) |

This study supports that compositions of the present invention have improved pharmacokinetic and/or pharmacodynamic time action.

Insulin Lispro Formulated with 10 μg/mL Treprostinil and Either 15 or 25 mM Citrate A study on compositions comprising 10 μg/mL treprostinil and either 15 or 25 mM citrate is performed in diabetic (Alloxan induced), castrated, male Yucatan miniature swine (average age 33 months, average body weight 49 kgs) following generally the procedures described above.

Test articles (Compositions N and O in the table below) are formulated by adding the indicated amounts of citrate, treprostinil, NaCl and MgCl$_2$ to a vial of Humalog®. As with the study described above, the necessary quantity of treprostinil is withdrawn from a vial of 1 mg/mL Remodulin®, so the addition of treprostinil to the test compositions also results in the addition of small quantities of m-cresol, sodium citrate and sodium chloride, as well as a slight dilution of the Humalog® excipients. Such small quantities are not believed to affect the properties of the compositions, however, and are thus not reflected in Table 10 below.

TABLE 10

| Name | Formulation Composition |
| --- | --- |
| Composition N | 99.5 U/ml Insulin lispro<br>10 μg/ml treprostinil<br>15 mM citrate<br>5 mM MgCl$_2$<br>15 mM NaCl<br>16 mg/ml glycerin |
| Composition O | 99.6 U/ml insulin lispro<br>10 μg/ml treprostinil<br>25 mM citrate<br>5 mM MgCl$_2$<br>15 mM NaCl<br>16 mg/ml glycerin |
| Humalog ® | 100 U/mL KPB<br>1.88 mg/mL dibasic sodium phosphate<br>16 mg/mL glycerol<br>3.15 mg/mL meta-cresol<br>0.3 mM zinc<br>pH 7.4 |

Study is designed as a 20 pig full cross-over design in which each pig is studied on each test article. One animal does not participate in Composition N group due to port non-patency or low baseline glucose, data is n=19 for that group. Serum glucose data are represented in Table 11 below as mean (mg/dL)+/−SEM unless otherwise specified.

TABLE 11

| Time | Humalog ® | | Composition N | | Composition O | |
|---|---|---|---|---|---|---|
| (min) | AVG | SEM | AVG | SEM | AVG | SEM |
| −30 | 323.8 | 8.4 | 336.3 | 9.4 | 323.3 | 9.2 |
| −20 | 332.6 | 9.1 | 344.7 | 9.5 | 336.0 | 9.2 |
| 0 | 343.1 | 8.8 | 354.0 | 9.9 | 346.6 | 10.2 |
| 5 | 353.3 | 9.8 | 364.5 | 10.8 | 355.2 | 10.9 |
| 10 | 355.8 | 9.8 | 357.1 | 9.1 | 342.3 | 11.4 |
| 15 | 355.2 | 10.6 | 340.7 | 11.6 | 325.6 | 13.8 |
| 30 | 317.9 | 12.9 | 293.3 | 15.9 | 270.0 | 17.9 |
| 45 | 291.4 | 19.1 | 254.8 | 19.2 | 239.7 | 21.0 |
| 60 | 255.6 | 21.1 | 220.9 | 21.3 | 216.1 | 22.8 |
| 75 | 239.8 | 23.9 | 195.2 | 21.7 | 193.8 | 22.8 |
| 90 | 205.7 | 23.7 | 173.8 | 22.6 | 172.6 | 22.7 |
| 105 | 184.4 | 22.8 | 156.0 | 21.5 | 158.6 | 22.7 |
| 120 | 162.0 | 21.7 | 139.1 | 19.4 | 145.9 | 21.7 |
| 150 | 135.3 | 20.5 | 107.1 | 18.2 | 116.8 | 19.4 |
| 180 | 119.2 | 18.4 | 86.1 | 16.5 | 104.8 | 18.3 |
| 240 | 84.1 | 13.3 | 83.3 | 13.1 | 80.8 | 14.8 |
| 360 | 63.4 | 11.4 | 108.6 | 14.2 | 86.1 | 10.8 |

Collectively, the studies described above support that the compositions of the present invention have faster pharmacokinetic and/or pharmacodynamic action than commercial formulations of existing insulin analog products.

Stability Studies

The stability of insulin lispro when formulated with a range of citrate concentrations, treprostinil and other excipients is assessed. The compositions of exemplary formulations, shown in table 12 below, are prepared by formulating insulin lispro active pharmaceutical ingredient with the other excipients indicated.

TABLE 12

| Name | Composition |
|---|---|
| Composition P | 100 U/mL insulin lispro<br>15 mM citrate<br>10 μg/mL treprostinil<br>0.65 mM zinc<br>5 mM MgCl$_2$<br>0.06% Poloxamer 188<br>3.15 mg/mL m-cresol<br>17.5 mM Glycerol<br>pH 7.4 |
| Formulation Q | 100 U/mL insulin lispro<br>20 mM citrate<br>10 μg/mL treprostinil<br>0.65 mM zinc<br>6.6 mM MgCl$_2$<br>0.06% Poloxamer 188<br>3.15 mg/mL m-cresol<br>15.68 mM Glycerol<br>pH 7.4 |
| Formulation R | 100 U/mL insulin lispro<br>25 mM citrate<br>10 μg/mL treprostinil<br>8.3 mM MgCl$_2$<br>0.65 mM zinc<br>0.06% Poloxamer 188<br>3.15 mg/mL m-cresol<br>13.82 mM Glycerol<br>pH 7.4 |

The solutions are filtered using 50 ml Steriflip Vacuum filter with 0.22 μM PES membrane (Cat #: SCGP00525, EMD Millipore, Billerica, Md.) and distributed into either 10-mL vials with crimp-top or 3-mL glass insulin cartridges, then incubated at 4° C. and 30° C. respectively. The 4° C. samples are stored without agitation for 64 days, while the 30° C. samples are incubated without agitation for 36 days, followed by a simulated in-use period of 28 days. In the in-use simulation the container is inverted and a sample is drawn from each vial or cartridge three times a day for 28 days. Two draws are done at each time point on days before or after any Saturday, Sunday or holiday. Aliquots of 80 μL are drawn from each vial using Terumo U-100 insulin (½ cc 27 G×½") syringe and 30 μL are drawn from each cartridge using the HumaPen Luxura HD using the Comfort Point 6 mm (31 G×¼") needle.

Samples are collected from day 36 (day 1 of the in-use period at 30° C.), day 50 and day 64 to be analyzed using reversed-phase high-performance liquid chromatography (RP-HPLC) and analytical size exclusion chromatography (SEC).

All formulations are also evaluated in 3 mL glass insulin cartridges at 37° C. while shaking at ~100 rpm. This condition is intended to be indicative of stability in continuous subcutaneous insulin infusion therapy. Endpoint samples from this condition are analyzed using RP-HPLC and SEC.

RP-HPLC analysis is performed to assess protein purity in each formulation at the stability time points using a UV detector at 214 nm. Each sample (5 μL) is separated using a Zorbax 300SB-C18, Rapid Resolution 4.6×150 mm 3.5-Micron column (Part #863973-902) at 40° C. with a flow rate of 0.6 mL/minute and mobile phase A (50 mM sulfate, pH 2.3+20% acetonitrile (v/v)) and mobile phase B (50 mM sulfate, pH 2.3+50% acetonitrile (v/v)). Gradient of mobile phase B at 0, 3, 15, 21, 26, 27, 27.5 and 35.0 min is 21, 25, 25, 30, 80, 80, 21 and 21%, respectively. Insulin content is calculated using RP-HPLC by combining the integrations of the insulin main peak area and A21 area then dividing by an insulin lispro standard. Insulin loss for formulation samples compared to Humalog® control is less than 5% for all samples out to 64 days at 4° C. and 30° C. Percentage of sample outside of main peak with A21 is calculated by dividing chromatographic main peak area by total peak area and subtracting that area and A21 from 100. The percent outside of the main peak area is less than 1.76% for all samples at 4° C. for 64 days and less than 2.48% for all samples at 30° C. for 64 days.

For the SEC analysis, each sample (5 μL) is separated using a Sepax Zenix-C SEC-80, 7.8×300 mm, 3 μm particles column (catalog #233080-7830) at 5° C. and a flow rate of 1.0 mL/minute with isocratic elution of mobile phase (0.1% TFA, 50% ACN) over a run time of 25 minutes.

Percentage of high molecule weight polymer (% HMWP) is calculated by integrating the total percent area of all peaks eluting prior to the main peak. Results (% HMWP) are given in the tables below. HMWP formation is less than 1% for all samples out to 64 days at 4° C. and 30° C., and HMWP formation in citrate-containing samples is comparable to HMWP formation in Humalog® control samples.

TABLE 13

Vials stored at 4° C.: insulin content, units/mL.

| Composition | Day 36 | Day 50 | Day 64 |
|---|---|---|---|
| P | 100.07 | 99.89 | 99.36 |
| Q | 100.06 | 99.88 | 99.38 |
| R | 100.03 | 99.85 | 99.29 |

TABLE 14

Vials stored at 4° C.: other related substances, percent.

| Composition | Day 36 | Day 50 | Day 64 |
|---|---|---|---|
| P | 0.92 | 1.05 | 1.17 |
| Q | 0.93 | 1.07 | 1.12 |
| R | 0.96 | 1.09 | 1.32 |

TABLE 15

Vials stored at 4° C.: high molecular weight species, percent.

| Composition | Day 36 | Day 50 | Day 64 |
|---|---|---|---|
| P | 0.17 | 0.19 | 0.21 |
| Q | 0.16 | 0.20 | 0.22 |
| R | 0.16 | 0.20 | 0.21 |

TABLE 16

Vials stored at 30° C.: insulin content, units/mL.

| Composition | Day 36 | Day 50 | Day 64 |
|---|---|---|---|
| P | 98.77 | 98.60 | 98.47 |
| Q | 98.67 | 98.50 | 98.46 |
| R | 98.82 | 98.65 | 98.46 |

TABLE 17

Vials stored at 30° C.: other related substances, percent.

| Composition | Day 36 | Day 50 | Day 64 |
|---|---|---|---|
| P | 1.23 | 1.40 | 1.53 |
| Q | 1.33 | 1.50 | 1.54 |
| R | 1.18 | 1.35 | 1.54 |

TABLE 18

Vials stored at 30° C.: high molecular weight species, percent.

| Composition | Day 36 | Day 50 | Day 64 |
|---|---|---|---|
| P | 0.33 | 0.41 | 0.46 |
| Q | 0.29 | 0.39 | 0.43 |
| R | 0.29 | 0.38 | 0.43 |

TABLE 19

3-mL cartridges stored 14 days at 37° C. with shaking.

| Composition | % HMW | Units/ml | % Other Related Substances |
|---|---|---|---|
| P | 0.33 | 98.24 | 1.32 |
| Q | 0.34 | 97.88 | 1.54 |
| R | 0.30 | 97.66 | 1.59 |

An additional stability study is performed wherein formulations containing insulin lispro and different concentrations of citrate, treprostinil, zinc and other excipients are subjected to different conditions. Twenty-four formulations of citrate-containing formulations and two control formulations which do not contain citrate are prepared. The concentrations of citrate, magnesium chloride, Zn, total chloride, treprostinil and poloxamer in the formulations are indicated in Table 20 below.

TABLE 20

Formulations Tested

| No. | Citrate (mM) | MgCl$_2$ (mM) | Total Zn (mM) | Total Chloride (mM) | Treprostinil (μg/mL) | Poloxamer 188% |
|---|---|---|---|---|---|---|
| S | 0 | 0 | 0.3 | 10 | 0 | 0 |
| T | 0 | 0 | 0.3 | 20 | 0 | 0 |
| U | 12 | 2.5 | 0.4 | 10 | 2 | 0 |
| V | 12 | 2.5 | 0.8 | 13 | 0 | 0 |
| X | 12 | 7.5 | 0.4 | 20 | 0 | 0 |
| Y | 12 | 7.5 | 0.8 | 23 | 2 | 0 |
| Z | 15 | 5 | 0.6 | 20 | 1 | 0 |
| AA | 18 | 2.5 | 0.4 | 10 | 0 | 0 |
| BB | 18 | 2.5 | 0.8 | 13 | 2 | 0 |
| CC | 18 | 7.5 | 0.4 | 20 | 2 | 0 |
| DD | 18 | 7.5 | 0.8 | 23 | 0 | 0 |
| EE | 15 | 5 | 0.6 | 16 | 1 | 0.045 |
| FF | 15 | 5 | 0.6 | 16 | 1 | 0.045 |
| GG | 15 | 5 | 0.6 | 25 | 1 | 0.045 |
| HH | 15 | 5 | 0.6 | 30 | 1 | 0.045 |
| II | 15 | 5 | 0.6 | 50 | 1 | 0.045 |
| JJ | 15 | 5 | 0.6 | 100 | 1 | 0.045 |
| KK | 15 | 5 | 0.6 | 20 | 1 | 0.06 |
| LL | 12 | 2.5 | 0.4 | 10 | 0 | 0.09 |
| MM | 12 | 2.5 | 0.8 | 13 | 2 | 0.09 |
| NN | 12 | 7.5 | 0.4 | 20 | 2 | 0.09 |
| OO | 12 | 7.5 | 0.8 | 23 | 0 | 0.090 |
| PP | 18 | 2.5 | 0.4 | 10 | 2 | 0.09 |
| QQ | 18 | 2.5 | 0.8 | 13 | 0 | 0.09 |
| RR | 18 | 7.5 | 0.4 | 20 | 0 | 0.090 |
| SS | 18 | 7.5 | 0.8 | 23 | 2 | 0.090 |

In order to prepare the formulations, a lispro concentrate stock solution is prepared containing 200 units insulin lispro/mL, 24.2 mg glycerin/mL, 6.30 mg metacresol/mL, and 0.6 mM zinc in water for bulk sterile operations. This stock solution is pH adjusted with hydrochloric acid to dissolve the insulin lispro and then adjusted with sodium hydroxide to pH of 7.40.

The citrate-containing formulations are prepared by diluting the lispro concentrate with the appropriate volumes of excipient stock solutions: sodium citrate, magnesium chloride, zinc oxide, treprostinil, and poloxamer 188. To achieve target chloride content, a stock solution of sodium chloride is added to some formulations. The solution is pH adjusted to 7.30-7.50 with hydrochloric acid or sodium hydroxide followed by q.s. with water for bulk sterile operations.

The non-citrate formulations are prepared by diluting the lispro concentrate with the appropriate volumes of water for bulk sterile operations or water for bulk sterile operations and sodium chloride solution. The solution is pH adjusted to 7.30-7.50 with hydrochloric acid or sodium hydroxide followed by q.s. with water for bulk sterile operations.

The formulations are sterile filtered and then volumetrically transferred to 10 mL glass vials with a 10.3 mL fill, stoppered, and crimp sealed. Twenty vials are filled per batch.

The study includes subjecting vials of each formulation to one of three different conditions, as described below.

TABLE 21

| Condition | Description |
| --- | --- |
| Control (n = 5) | 5° C. static upright storage for 39 days |
| Thermal stress (n = 5) | Abbreviated shipping stress simulation followed by 30° C. static upright storage for 32 days |
| Cumulative Stress (n = 5) | Abbreviated shipping stress simulation followed by 32 day simulated patient in-use with 30° C. upright storage between dosing |

As indicated in the table above, the thermal stress and cumulative stress conditions include first subjecting the vials to an abbreviated shipping stress simulation, which is performed as described in International Safe Transit Association (ISTA) Procedure 3A (2008). For the thermal stress condition, the vials are then placed into static upright storage at 30° C. For the cumulative stress condition, the vials are then subjected to a patient in-use simulation. The patient in-use simulation is performed by withdrawing 8 units of air into any insulin syringe, inserting the needle into the vial while the vial is in the upright position, ensuring that the needle tip does not touch the insulin solution, injecting air into the vial, inverting the vial and syringe, withdrawing 8 units of the product solution, eliminating any air bubbles in the syringe by slowly moving the plunger to push the bubble back into the vial (repeating if necessary) and adjusting the syringe plunger so that the final dosage is 8 units, removing the syringe, and placing the vial back into the 30° C. incubator. This process is repeated for three doses per day for 32 days. When not being dosed, the vials are stored upright at 30° C.

Chemical stability is tested by size exclusion chromatography (SEC) and reverse phase HPLC (RP-HPLC). RP-HPLC analysis is performed to assess protein purity in each formulation using a UV detector at 214 nm. Each sample (5 µL) is separated using a Halo Peptide ES-C18, 4.6×150 mm 2.7-Micron column (Part #92124-702) at 40° C. with a flow rate of 1.0 mL/minute and mobile phase A (50 mM sulfate, pH 2.3+20% acetonitrile (v/v)) and mobile phase B (50 mM sulfate, pH 2.3+50% acetonitrile (v/v)). Gradient of mobile phase B at 0, 2, 17, 22, 25, 29, 29.5, and 35 minutes is 25, 25, 27, 40, 90, 90, 25 and 25%, respectively. Insulin content is calculated by combining the integrations of the insulin main peak and B3 peak areas then dividing by an insulin lispro standard. For SEC, each sample (50 µL) is separated using a Sepax Zenix-C SEC-80, 7.8×300 mm, 3 µm particles column (catalog #233080-7830) at 5° C. and a flow rate of 1.0 mL/minute with isocratic elution of mobile phase (0.1% TFA, 50% ACN) over a run time of 25 minutes. Percentage of high molecule weight polymer (% HMWP) is calculated by integrating the total percent area of all peaks eluting prior to the main peak. One vial each from formulations PP and QQ subjected to the cumulative stress conditions could not be sampled due to particulate formation. All other vials were tested, and all results were within insulin lispro acceptance criteria for both potency (95-105 U/mL) and HMWP (NMT 1.5%).

Physical stability is assessed by visual appearance testing in which samples are visually inspected. Samples are graded as pass that are clear, colorless, and essentially free of visible particles. All samples of all formulations pass visual appearance testing at all time points in the control and thermal stress conditions. Visual appearance testing results for the cumulative stress condition are provided in table 22 below.

TABLE 22

| Formulation | 21 Days (n = 5) | 24 Days (n = 5) | 28 Days (n = 5) | 32 Days (n = 5) |
| --- | --- | --- | --- | --- |
| S | 100% Pass | 100% Pass | 100% Pass | 100% Pass |
| T | 100% Pass | 100% Pass | 80% Pass | 100% Pass |
| U | 100% Pass | 100% Pass | 100% Pass | 100% Pass |
| V | 100% Pass | 100% Pass | 100% Pass | 100% Pass |
| X | 100% Pass | 100% Pass | 100% Pass | 100% Pass |
| Y | 100% Pass | 100% Pass | 100% Pass | 100% Pass |
| Z | 100% Pass | 100% Pass | 100% Pass | 100% Pass |
| AA | 100% Pass | 100% Pass | 100% Pass | 100% Pass |
| BB | 100% Pass | 100% Pass | 100% Pass | 100% Pass |
| CC | 100% Pass | 100% Pass | 100% Pass | 100% Pass |
| DD | 100% Pass | 100% Pass | 100% Pass | 100% Pass |
| EE | 100% Pass | 100% Pass | 40% Pass | 0% Pass |
| FF | 100% Pass | 100% Pass | 100% Pass | 0% Pass |
| GG | 100% Pass | 80% Pass | 0% Pass | 0% Pass |
| HH | 100% Pass | 100% Pass | 0% Pass | 0% Pass |
| II | 100% Pass | 100% Pass | 0% Pass | 0% Pass |
| JJ | 100% Pass | 100% Pass | 0% Pass | 0% Pass |
| KK | 100% Pass | 100% Pass | 0% Pass | 0% Pass |
| LL | 60% Pass | 60% Pass | 40% Pass | 0% Pass |
| MM | 100% Pass | 100% Pass | 100% Pass | 20% Pass |
| NN | 100% Pass | 100% Pass | 100% Pass | 80% Pass |
| OO | 100% Pass | 100% Pass | 100% Pass | 100% Pass |
| PP | 20% Pass | 0% Pass | 0% Pass | 0% Pass |
| QQ | 80% Pass | 80% Pass | 20% Pass | 0% Pass |
| RR | 100% Pass | 100% Pass | 100% Pass | 0% Pass |
| SS | 100% Pass | 100% Pass | 100% Pass | 0% Pass |

All vials of formulations U, V, X, Y, Z, AA, BB, CC DD and OO pass the cumulative stress testing through day 32 of the patient in-use simulation. All vials of formulations FF, MM, NN, RR and SS pass the cumulative stress testing out through day 28. All vials of formulations EE, HH, II, JJ and KK pass through day 24. All vials of formulation GG pass out through day 21.

The studies described above support that the compositions are chemically and physically stable under refrigerated and thermal stress conditions, and that certain compositions of the present invention are sufficiently stable for commercial use even under simulated in use testing out to 32 days.

Sequences

```
Human insulin A-chain
                                          (SEQ ID NO: 1)
Gly Ile Val Glu Gln Cys Cys Thr Ser Ile Cys
Ser Leu Tyr Gln Leu Glu Asn Tyr Cys Asn.

Human insulin B-chain
                                          (SEQ ID NO: 2)
Phe Val Asn Gln His Leu Cys Gly Ser His Leu
Val Glu Ala Leu Tyr Leu Val Cys Gly Glu Arg
Gly Phe Phe Tyr Thr Pro Lys Thr.

Insulin lispro B-chain
                                          (SEQ ID NO: 3)
Phe Val Asn Gln His Leu Cys Gly Ser His Leu
Val Glu Ala Leu Tyr Leu Val Cys Gly Glu Arg
Gly Phe Phe Tyr Thr Lys Pro Thr.

Insulin aspart B-chain
                                          (SEQ ID NO: 4)
Phe Val Asn Gln His Leu Cys Gly Ser His Leu
Val Glu Ala Leu Tyr Leu Val Cys Gly Glu Arg
Gly Phe Phe Tyr Thr Asp Lys Thr.

Insulin glulisine B-chain
                                          (SEQ ID NO: 5)
Phe Val Lys Gln His Leu Cys Gly Ser His Leu
Val Glu Ala Leu Tyr Leu Val Cys Gly Glu Arg
Gly Phe Phe Tyr Thr Pro Glu Thr.
```

We claim:

1. A pharmaceutical composition comprising:
   a. an insulin;
   b. citrate, in a concentration from about 5 to about 25 mM;
   c. treprostinil, in a concentration from about 0.04 to about 20 μg/mL;
   d. a preservative; and
   e. zinc, in a concentration sufficient to provide at least 2 zinc ions per six molecules of insulin;
   and having a pH of about 7.0 to about 7.8 at room temperature, wherein the pharmaceutical composition provides for an uptake of insulin into the blood, as measured by early ½ Tmax, that is at least 20% more rapid than for compositions which contain the same insulin but which do not contain citrate or treprostinil; and wherein the composition does not comprise EDTA.

2. The pharmaceutical composition of claim 1 wherein the zinc concentration is from about 0.2 to about 2 mM.

3. The pharmaceutical composition of claim 1, wherein the zinc concentration is from about 0.6 to about 0.8 mM.

4. The pharmaceutical composition of claim 3, further comprising magnesium chloride.

5. The pharmaceutical composition of claim 4 wherein the concentration of magnesium chloride is about 5 mM.

6. The pharmaceutical composition of claim 5 wherein the insulin is insulin lispro.

7. The pharmaceutical composition of claim 6 wherein the insulin lispro is present in a concentration from about 100 to about 200 U/mL.

8. The pharmaceutical composition of claim 7 further comprising glycerol.

9. The pharmaceutical composition of claim 8 wherein the concentration of glycerol is about 12 mg/mL.

10. The pharmaceutical composition of claim 9 wherein the preservative is m-cresol.

11. The pharmaceutical composition of claim 10 wherein the concentration of m-cresol is about 3.15 mg/mL.

12. The pharmaceutical composition of claim 11 wherein the pharmaceutical composition is stable for up to 28 days at temperatures of up to 30° C.

13. The pharmaceutical composition of claim 1 wherein the pharmaceutical composition does not contain any additional vasodilatory agent.

14. The pharmaceutical composition of claim 1 wherein the pharmaceutical composition does not contain any oligosaccharides.

15. The pharmaceutical composition of claim 1 wherein:
    a. the insulin is insulin lispro, and is present in a concentration from about 100 to about 200 U/mL;
    b. citrate is in a concentration of about 15 mM;
    c. treprostinil is in a concentration of about 1 μg/mL;
    d. the preservative is m-cresol, and is present in a concentration of about 3.15 mg/mL; and
    e. zinc is in a concentration from about 0.6 to about 0.8 mM;
    and wherein the pharmaceutical composition further comprises:
    f. glycerol, in a concentration of about 12 mM; and
    g. magnesium chloride, in a concentration of about 5 mM;
    and wherein the pharmaceutical composition does not contain EDTA, any additional vasodilatory agents or any oligosaccharides;
    and wherein the pharmaceutical composition provides for an uptake of insulin into the blood, as measured by early ½ Tmax, that is at least 20% more rapid than for compositions which contain the same insulin but which do not contain citrate or treprostinil;
    and wherein the pharmaceutical composition is stable for (i) at least 24 months at 2-8° C., and (ii) up to 28 days at temperatures of up to 30° C.

16. A method of treating diabetes comprising administering to a human in need thereof an effective dose of the pharmaceutical composition of claim 1.

17. An article of manufacture comprising the pharmaceutical composition of claim 1.

18. The article of manufacture of claim 17 which is a multi-use vial.

19. The article of manufacture of claim 17 which is a multi-use cartridge.

20. The article of manufacture of claim 17 which is a re-usable pen injector.

21. The article of manufacture of claim 17 which is a disposable pen device.

22. The article of manufacture of claim 17 which is a pump device for continuous subcutaneous insulin infusion therapy.

* * * * *

UNITED STATES PATENT AND TRADEMARK OFFICE
CERTIFICATE OF CORRECTION

PATENT NO.         : 10,925,931 B2
APPLICATION NO.    : 15/868272
DATED              : February 23, 2021
INVENTOR(S)        : Michael Patrick Akers et al.

Page 1 of 1

It is certified that error appears in the above-identified patent and that said Letters Patent is hereby corrected as shown below:

In the Specification

Column 1 Line 5: Delete "2019," and insert -- 2016, --, therefor.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*